United States Patent
Huang et al.

(10) Patent No.: US 11,207,447 B2
(45) Date of Patent: Dec. 28, 2021

(54) METHOD FOR PREPARING AN ANIMAL DECELLULARIZED TISSUE MATRIX MATERIAL AND A DECELLULARIZED TISSUE MATRIX MATERIAL PREPARED THEREBY

(71) Applicant: Beijing Ruijian Gaoke Biotechnology Co., Ltd., Beijing (CN)

(72) Inventors: Senli Huang, Beijing (CN); Wenquan Sun, Beijing (CN)

(73) Assignee: Beijing Ruijian Gaoke Biotechnology Co., Ltd., Beijing (CN)

( * ) Notice: Subject to any disclaimer, the term of this patent is extended or adjusted under 35 U.S.C. 154(b) by 230 days.

(21) Appl. No.: 16/545,338

(22) Filed: Aug. 20, 2019

(65) Prior Publication Data
US 2019/0374679 A1     Dec. 12, 2019

Related U.S. Application Data

(63) Continuation-in-part of application No. 14/914,283, filed as application No. PCT/CN2014/078737 on May 29, 2014, now Pat. No. 10,426,868.

(30) Foreign Application Priority Data

Aug. 26, 2013   (CN) .......................... 201310376619.8

(51) Int. Cl.
*A61L 27/36*   (2006.01)
*A61L 27/58*   (2006.01)

(52) U.S. Cl.
CPC ......... *A61L 27/3687* (2013.01); *A61L 27/362* (2013.01); *A61L 27/3691* (2013.01); *A61L 27/58* (2013.01); *A61L 2430/34* (2013.01); *A61L 2430/40* (2013.01)

(58) Field of Classification Search
None
See application file for complete search history.

(56) References Cited

U.S. PATENT DOCUMENTS

2008/0195229 A1   8/2008   Quijano et al.

FOREIGN PATENT DOCUMENTS

| CN | 101011604 A | 8/2007 |
|---|---|---|
| CN | 101366975 A | 2/2009 |
| CN | 101884810 A | 11/2010 |
| CN | 103432627 A | 12/2013 |
| JP | 2012508599 A | 4/2012 |
| WO | 0148153 A1 | 7/2001 |
| WO | 2011132089 A2 | 10/2011 |
| WO | 2012003450 A2 | 1/2012 |
| WO | 2012149253 A1 | 11/2012 |
| WO | 2013009595 A2 | 1/2013 |

OTHER PUBLICATIONS

Keane et al. "Methods of tissue decellularization used for preparation of biologic scaffolds and in vivo relevance." Methods 84 (2015): 25-34. (Year: 2015).*
International Search Report of PCT/CN2014/078737, dated Sep. 2, 2014.
Anil Srivastava et al, Use of Porcine Acellular Dermal Matrix as a Dermal Substitute in Rats, Annals of Surgery, Jan. 1, 2001, pp. 400-408.
Ehab Kheir et al: Development and Characterization of an accellular porcine cartilage bone matrix for use in tissue engineering. Journal of NBiomedical Matgerials Research Part A, vol. 99A, No. 2, Nov. 19, 2011, pp. 283-294.
Daniel W. Youngstrom et al: Functional Characterization of Detergent-Decellularized Equine Tendon Extracellular Matrix for Tissue Engineering Applications, Plos One, vol. 8, No. 5, May 27, 2013, p. e64151, XP055350763.
Peter M. Crapo et al: "An overview of tissue and whole organ decewllularization processes", Biomaterials, Elsevier Science Publishers BV, Barking, GB, vol. 342, No. 12, Jan. 19, 2011, pp. 3233-3243.
Supplementary European Search Report of EP14840537, dated Mar. 2, 2017.
U.S Appl. No. 14/914,283, filed Feb. 25, 2016.

* cited by examiner

*Primary Examiner* — Emily A Cordas
(74) *Attorney, Agent, or Firm* — Banner & Witcoff, Ltd.

(57) ABSTRACT

A method for manufacturing an animal acellular tissue matrix material and a tissue matrix material manufactured by the same. The tissue matrix material manufactured by the method retains an original basic scaffold structure of a tissue extracellular matrix, with an antigen causing immunological rejection in a human body being effectively removed from the animal tissue. An animal dermal matrix manufactured by the method retains the biological integrity of a natural dermal tissue matrix and can be used for restoration and repair of lesion and missing tissues.

19 Claims, 16 Drawing Sheets

METHOD FOR PREPARING AN ANIMAL DECELLULARIZED TISSUE MATRIX MATERIAL AND A DECELLULARIZED TISSUE MATRIX MATERIAL PREPARED THEREBY

CROSS-REFERENCE TO RELATED APPLICATIONS

This is a continuation-in-part of application Ser. No. 14/914,283, filed on Feb. 25, 2016, entitled "Method for Preparing an Animal Decellularized Tissue Matrix Material and a Decellularized Tissue Matrix Material Prepared thereby", which is a national stage application under 35 U.S.C. 154 (d)(4) and 35 U.S.C. 371 for PCT/CN2014/078737, filed on May 29, 2014 and claimed priority under 35 U.S.C. 119(a) and 35 U.S.C. 365(b) to Chinese Patent Application No. 201310376619.8, filed on Aug. 26, 2013, the entire disclosures of the foregoing applications being incorporated herein by reference.

TECHNICAL FIELD

The present invention relates to the technical field of treatment of biological tissues and manufacture of tissue matrix materials, and in particular relates to a method for manufacturing an animal acellular tissue matrix material and an acellular tissue matrix material manufactured by the same.

BACKGROUND OF THE RELATED ART

There are great similarity and homology in an extracellular matrix of a tissue and organ of a human body and many animals. A biological matrix material manufactured by decellularization of an allogeneic or xenogenic tissue and organ has been successfully used for the repair and restoration of human tissues in clinical medicine. The decellularized tissue and organ matrix is also widely used for various studies in tissue engineering and regenerative medicine, for example, removing original cell components of a tissue and organ of animals, and re-cellularizing and functionalizing the matrix of the tissue and organ having a three-dimensional tissue scaffold structure by human cells in vitro, thereby finally producing the tissue and organ which can be implanted to human body.

The matrix of the tissue and organ is a three-dimensional scaffold composed of various complex structural proteins and functional proteins, and comprises many other active complexes. Main components include collagenous fiber, glycoprotein, mucoprotein, and the like, and the other components include saccharides such as glycosaminoglycan (hyaluronic acid, chondroitin sulfate), some lipids and growth factors. A good matrix of the tissue and organ has suitable biomechanical strength, and after being implanted into a host, the matrix material provides initial biomechanical support, and regulates cell behavior (e.g., adherence, migration, proliferation and differentiation) by interacting with a host cell, and the matrix of the tissue and organ itself is gradually degraded and converted into a new tissue with the ingrowth of the host cell.

Currently, there are approximately thirty kinds of matrix material products derived from tissues and organs all over the world, which have been used in various clinical medicines such as tissue repair and regeneration. Raw materials of the tissues and organs in these products are derived from tissues of human and various mammals, including blood vessel, cardiac valve, ligament, nerve, skin, small intestinal mucosa, forestomach, pericardium, peritoneum, muscle tendon and bladder, and the like.

A process procedure for manufacturing the matrix of the tissue and organ is very complex, including processes such as collection, preservation, washing, disinfection, decellularization, antigenicity reduction, virus inactivation, and terminal sterilization of the tissue and organ, and the like. There are many existing methods for manufacturing the matrix of the tissue and organ, and they can be classified into a physical method, a chemical method, an enzymatic method and the like according to their action principles of the decellularization. The most commonly used decellularization method is a method in which the physical treatment and chemical treatment are combined. The cellular membrane is damaged by stirring or ultrasonic, mechanical massage or pressurization, freezing and thawing, so that the cell components are released from the cell, further facilitating the subsequent decellularization and washing using a chemical detergent. The physical method itself is generally not sufficient to achieve complete decellularization. Enzymatic treatment method, such as the use of trypsin, can alter the density and porosity of the tissue extracellular matrix, and cut the connection between the cell surface and the tissue extracellular matrix. In addition, by using different process procedures and methods, the removal efficiency of cells and the effect or damage to the matrix of the tissue and organ are different. In addition to direct damage to the matrix of the tissue and organ, the collection, preservation, washing, disinfection, and decellularization treatment also influence the subsequent processing steps of the tissue and organ. Various treatments will influence and change the biochemical composition of the matrix of the tissue and organ, and the ultrastructure and biomechanical property of the three-dimensional scaffold to different extent, which will influence the response of the host to the implanted matrix material. The evidence of preclinical animal tests and human clinical application demonstrates that there are great differences among various products of the matrix of the tissue and organ in terms of the clinical performance of tissue repair and regeneration. The variation of characteristics of the matrix of the tissue and organ during the manufacture process is one of the main reasons causing the difference of clinical effects of various products.

Content of the Invention

In one aspect, the present invention provides a method for manufacturing an animal acellular tissue matrix material, which comprises the steps of:

(1). collecting a raw material of an animal tissue, wherein the animal tissue is washed to remove blood and dirt, and cut into a tissue material having a length, a width and a height of the desired specification and dimension, and then the tissue material is preserved at a low temperature;

(2). thawing slowly, and rehydrating the tissue material in a normal saline containing gentamicin;

(3). disinfecting and sterilizing the tissue material in a moderate alkaline solution, wherein the tissue material is then rinsed with sterile pure water, and the pH of the tissue material is adjusted to be neutral;

(4). decellularizing and washing the tissue material;

(5). digesting DNA components of the animal tissue, wherein the animal tissue is then rinsed with a normal saline;

(6). digesting α-Gal antigen of the animal tissue, wherein the animal tissue is then rinsed with a high concentration of a sodium chloride solution, and rinsed with a normal saline;

(7). inactivating the viruses in the animal tissue the animal tissue, wherein the animal tissue is then rinsed with a phosphate buffer solution;

(8). packaging and sealing the animal tissue under an aseptic condition;

(9). terminal sterilization treatment.

In the method, an enzymatic method is used to remove cell components and α-Gal antigen and improve the pliability of a tissue scaffold.

In an embodiment of the present invention, the raw material of the animal tissue in step (1) is selected from skin, dermis, artery, vein, stomach, cartilage, meniscus, small intestine, large intestine, diaphragm, muscle tendon, ligament, nervous tissue, bladder, urethra and ureter.

In an embodiment of the present invention, the washing of the animal tissue to remove blood and dirt in step (1) is performed by using pure water and a physical method or ultrasonic washing.

In a process method for manufacturing the tissue matrix material, the step of preservation of a raw material of a porcine dermis at a low temperature is involved, wherein, the rate of cooling and heating is a very important parameter. If the rate of cooling and heating is too rapid or not uniform within the tissues, tiny cracks can occur in local regions of the tissues and the tissue matrix is prone to be tore when used.

In an embodiment of the present invention, preferably, the tissue material in step (1) is preserved at a temperature of −40° C. or less which is achieved with an average cooling rate of no more than 1.0° C. per minute, and more preferably, the cooling rate is 0.5° C. per minute. The tissue material preserved at a low temperature is slowly thawed in an environment of 5° C. to 12° C. in step (2), to avoid the production of cracks in the tissue due to an over-rapid temperature increase. After the ice is completely melted, the thawed tissue material is rehydrated in a normal saline containing 100 mg of gentamicin per litre for 3 hours to 6 hours in step (2).

In one embodiment of the present invention, the preservation at a low temperature in step (1) is long-term preservation, the method is to lay a porcine dermal material on a piece of protective layer with slightly larger area, such as cotton yarn cloth, paper, plastic film, nylon net or other cloth fabrics, and roll the dermis and the protective layer into one multilayer concentric roll or form a multilayer package form with the dermis and the protective layer being alternated, which is placed into a plastic bag, and kept in a refrigerator at −80° C. or −40° C. for preservation after being sealed.

In the preparation method of embodiments of the present invention, the initial disinfection and sterilization of a raw material of a porcine dermis are involved. The existing methods comprise use of sodium hypochlorite, peroxyacetic acid, hydrogen peroxide, iodine solution, and a high concentration of sodium hydroxide solution (with a pH of 13 or more). After the treatment using these solutions, the tissue matrix is damaged to different extent, especially with the effects of sodium hydroxide, sodium hypochlorite, and iodine solution being greater.

Unlike the disinfection and sterilization technology of the raw material in the existing methods, in an embodiment of the present invention, the moderate alkaline solution in step (3) is a sodium bicarbonate, or sodium hydroxide solution with a pH of 10.5 to 11.5 or an ammonia hydroxide solution with a concentration of 0.1%, the disinfection and sterilization method is to soak the rehydrated tissue material in the moderate alkaline solution for 24 hours to 48 hours with shaking slowly, thereby avoiding the damage of the tissue matrix.

In an embodiment of the present invention, the decellularization method in step (4) is to firstly rinse the disinfected and sterilized and rinsed tissue material in a normal saline containing 2.0 mmol/L of calcium chloride, 2.0 mmol/L of magnesium chloride and 100 mg/L of gentamicin at room temperature for 1 hours to 3 hours, and then add a dispase solution to elute cells.

In one embodiment of the present invention, the dispase solution is a neutral dispase solution, which contains 1 mmol/L to 20 mmol/L of calcium chloride, 1 mmol/L to 20 mmol/L of magnesium chloride and 50 units/L to 400 units/L of dispase, and the method for eluting cells with the dispase solution is to soak the tissue material in the neutral dispase solution, at 37° C. for 24 hours to 36 hours with shaking slowly, and more preferably, the neutral dispase solution contains 2.0 mmol/L of calcium chloride, 2.0 mmol/L of magnesium chloride and 100 units/L to 200 units/L of dispase.

In one embodiment of the present invention, after completing the decellularization in step (4), the washing step is performed. The washing comprises washing with a first detergent and washing with a second detergent, wherein the first detergent solution is prepared by dissolving polyethylene glycol tert-octylphenyl ether TRITON' X-100, at a concentration of 0.5%, in a buffer solution of hydroxyethylpiperazine ethane sulfonic acid (pH 7.0~8.0), and the washing method is to soak the tissue material in the first detergent solution at 37° C. for 12 hours to 18 hours with shaking slowly. The second detergent solution is prepared by dissolving-sodium deoxycholate, at a concentration of 1.0%, in a phosphate buffer solution (pH 7.2~7.8), and the washing method is to soak the tissue material in the second detergent solution at room temperature for 24 hours to 36 hours with shaking slowly. Meanwhile, other suitable detergents, such as TWEEN™-20 (polysorbate 20), t-octylphenoxyl polyethylene ethoxyethanol and 3-[(3-cholesterol aminopropyl)dimethylamino]-1-propanesulfonic acid, and the like, are used in embodiments of the present invention.

In an embodiment of the present invention, after being soaked in the first detergent solution and the second detergent solution, and prior to step (5), the tissue material is rinsed three times with a buffer solution of 20 mmol/L of hydroxyethylpiperazine ethane sulfonic acid (with a pH between 7.0~8.0) at room temperature, each time for 2 hours to 4 hours.

Due to the existence of DNA of the animal tissues, an inflammatory response is easily caused by the tissue matrix being implanted into a human body. In addition to human and old world monkeys, other mammals all contain α-Gal antigen consisting of glycoprotein or glycolipid with a disaccharide end of α-1,3-galactose residue [Galα(1,3)Gal] in vivo. In particular, the α-Gal antigen in porcine tissues will cause immunological rejection response. One of the methods for eliminating or overcoming the inflammatory response and rejection response is to remove DNA and α-Gal antigen from the animal tissue matrix using specific enzymatic treatment.

In an embodiment of the present invention, the digestion of DNA components of the animal tissue in step (5) is accomplished by adding a deoxyribonuclease solution, wherein the deoxyribonuclease solution is prepared by adding 2.0 mmol/L of calcium chloride, 2.0 mmol/L of magnesium chloride and 5000 enzyme units/L of deoxyribonuclease into a buffer solution of 100 mmol/L of trihydroxymethyl aminomethane-hydrochloric acid with a pH of 7.2, and a method for digesting DNA from the animal tissue is to soak the tissue material in the deoxyribonuclease solution to be treated for 18 hours to 28 hours at 37° C. with shaking slowly, and then place the tissue material in a normal saline to be rinsed twice at room temperature, each time for 1 hours to 3 hours.

In an embodiment of the present invention, digesting α-Gal antigen of the animal tissue in step (6) is accomplished by adding α-galactosidase solution, wherein the α-galactosidase solution is prepared by adding 2.0 mmol/L of calcium chloride, 2.0 mmol/L of magnesium chloride and an amount of 400 GALU units/L of α-galactosidase into a buffer solution of 10 mmol/L of hydroxyethylpiperazine ethane sulfonic acid with a pH between 7.0 and 8.0, and a method for digesting the α-Gal antigen of the animal tissue is to soak the tissue material in the α-galactosidase solution, to be washed for 24 hours to 36 hours, for example at 37° C. with shaking slowly.

When the tissue matrix implanted into human body is manufactured, it is necessary to remove various residual enzymes. To achieve the above objectives, in an embodiment of the present invention, the washing is performed using a salting-out method, wherein the high concentration of sodium chloride solution in step (6) is a 2% to 5% sodium chloride solution, and a rinsing method is to soak the tissue material in the sodium chloride solution and wash the tissue material twice at room temperature, each time for 2 hours to 4 hours. In one embodiment, the high concentration of sodium chloride solution can be a 3% sodium chloride solution. Furthermore, the sodium chloride solution can be replaced with other neutral salt solution, such as potassium chloride, magnesium chloride and lithium chloride, and the like.

To increase the safety of the products, in an embodiment of the present invention, said method also relates to a virus inactivation treatment, wherein the virus inactivation agents used in step (7) are hydrogen peroxide and peroxyacetic acid, and a method for the virus inactivation is to soak the tissue material in a solution containing 0.01% to 0.10% hydrogen peroxide, 0.05% to 0.50% acetic acid and 0.05% to 0.50% peroxyacetic acid, to be washed for 2 hours to 3 hours at room temperature with shaking slowly. In another embodiment of the present invention, a solution containing 0.02% hydrogen peroxide, 0.15% acetic acid and 0.10% peroxyacetic acid is used for virus inactivation, with the number of viruses being decreased by $10^6$ or more during 2 hours to 3 hours. The concentration of hydrogen peroxide, acetic acid and peroxyacetic acid may be varied with the number of bacteria.

In an embodiment of the present invention, after the virus inactivation in step (7), the tissue material is rinsed three times at room temperature with a neutral phosphate buffer solution, each time for 2 hours to 4 hours, to remove the residual hydrogen peroxide, acetic acid and peroxyacetic acid.

The terminal sterilization treatment of the tissue product is often one of the most destructive steps for the tissue material. For this reason, in an embodiment of the present invention, a low temperature irradiation is used to perform the treatment in step (9). In another embodiment of the present invention, under the condition of −40° C., the terminal sterilization treatment of the tissue material is performed using 10 kGy to 50 kGy gamma ray, which greatly reduces the damage to the tissue material. In some embodiments of the present invention, a radiation dosage is varied depending on the number of bacteria in the tissue matrix. In another embodiment, the terminal sterilization treatment of the tissue material is performed using 20 kGy to 30 kGy gamma ray.

In some alternative embodiments of the present invention, in addition to the irradiation terminal sterilization method, the tissue matrix in said method can also be sterilized by using ethylene oxide gas after being lyophilized.

In some embodiments of the present invention, the sequence of step (4) (decellularization with enzyme), step (5) (digesting DNA with enzyme) and step (6) (digesting α-1,3-galactose residue antigen with enzyme) can be adjusted or altered as actually required. For example, firstly, α-1,3-galactose residue antigen in animal tissues may be digested, and then the animal tissues are decellularized and the DNA components of animals are digested; or firstly, the animal DNA is eliminated, and then the α-1,3-galactose residue antigen is eliminated and finally treated by decellularization.

Furthermore, in some alternative embodiments of the present invention, if the animals improved by genetic engineering and free of α-Gal antigen are selected, step (6) is omitted and step (7) is directly performed. Meanwhile, to reduce the disadvantageous effect on the proteolysis of the extracellular matrix, the concentration of the dispase, temperature and time will be monitored and optimized while treating. In the process procedure, the specific enzyme inhibitor can further be added, for example, ethylenediamine tetraacetic acid, for inhibiting the activity of the dispase.

Another aspect of the present invention further relates to an animal acellular tissue matrix material manufactured by the above method of the embodiments of the present invention.

In one embodiment of the present invention, animal acellular tissue matrix material is obtained by using dermis with basement membrane or dermis with basement membrane removed as a raw material of an animal tissue.

In the method for manufacturing an acellular tissue matrix material according to the embodiments of the present invention, a series of steps of treating animal skin tissues and manufacturing the matrix of the tissue and organ as well as a plurality of biochemical solutions and formulas thereof are involved. The dermal tissue matrix material manufactured by the above steps and solutions retains the original basic scaffold structure of the tissue extracellular matrix, main biochemical components and biomechanical strength, with an antigen causing immunological rejection response in the human body being effectively removed from the animal tissue; and improves the flexibility, drapability and the integration performance of wound curved surface of the tissue matrix, and the manufactured animal dermis matrix is similar with human skin, which will not cause the collagen in the tissue matrix to crosslink with other proteins, and will not cause degradation or denaturation, and the decellularized dermis tissue retains the biological integrity of the natural dermal tissue matrix.

DETAILED DESCRIPTION OF EMBODIMENTS

Figure 1:
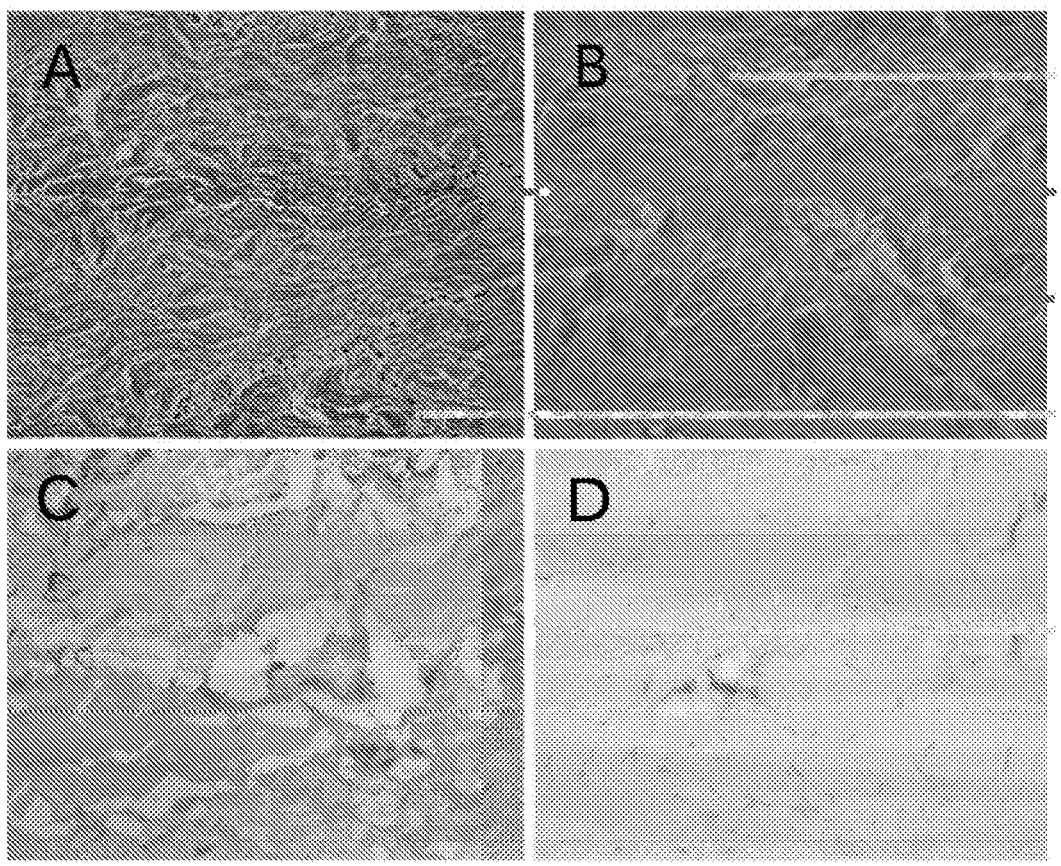
FIG. 1: Histology of tissue sections.
A: a HE staining section of a fresh porcine dermis;
B: a HE staining section of a dermal matrix after being treated;
C: an immunochemical staining section of α-1,3-galactose residue antigen of the fresh porcine dermis;
D: an immunochemical staining section of α-1,3-galactose residue antigen of the treated dermal matrix.

The embodiments of the present invention are further illustrated in detail by way of examples hereinafter, and intended to illustrate rather than to limit the present invention. Further, it should be noted by those skilled in the art that several improvements and modifications can be made to the present invention without departing from the principle of the present invention, and these improvements and modifications also fall within the protection scope of the present invention.

Example 1: Manufacture and Performance Detection of an Animal Acellular Tissue Matrix Material 1. Manufacture
(1) Collection and Preservation of a Tissue and Organ
Fresh porcine hide was collected from a newly slaughtered pig, and temporarily preserved in a refrigerator at 4° C. After the porcine hide was dehaired mechanically, the porcine hide was split into a dermis layer having a thickness of about 1.0 mm, which was cryopreserved at −20° C.
(2) Decellularization
After the dermis was thawed, it was firstly flushed with a normal saline twice, each time for 30 minutes. The flushed porcine dermis was soaked in a saline solution containing 100 mg of gentamicin per litre, and 2.0 millimole concentration of calcium chloride, 2.0 millimole concentration of magnesium chloride, and 150 units per litre of neutral dispase were further added to the solution, and the dermis is treated at 37° C. for 24 hours.
(3) Washing
After being soaked in gentamicin, the dermis was washed with a 0.5% polyethylene glycol tert-octylphenyl ether TRITON™ X-100 solution for 16 hours. After decellularization and washing, the dermis was flushed with a normal saline twice, each time for 120 minutes.
(4) Digestion of DNA and Removal of α-1,3-Galactose Residue Antigen
To each litre of the solution were further added 2.0 millimole concentration of calcium chloride, 2.0 millimole concentration of magnesium chloride, 5000 units of deoxyribonuclease and two tablets of BEANO® from GlaxoSmithkline (dietary supplement containing α-galactosidase), and the dermis was treated at room temperature for 20 hours.
(5) Virus Inactivation
After being washed, the dermis was sterilized and virus inactivated with a solution containing 0.02% hydrogen peroxide, 0.15% acetic acid and 0.10% peroxyacetic acid for 2 hours.
(6) Washing and Preservation
Finally, the dermis was flushed with sterile normal saline until no polyethylene glycol tert-octylphenyl ether TRITON™ X-100 and enzyme remained. The treated dermal matrix was temporarily preserved in 6% glycerin.

2. Performance Detection
It was indicated by measurements that the tensile strength of the material was 15.0±3.6 megapascal (N=24); the strength of the suture was 56±13 newton (N=24); each 100 g by wet weight of the dermis matrix contained 24.2±2.9 g of a dry matter material of a dermis (N=15).

It was showed by analysis using differential scanning calorimeter that the initial denaturation temperature of the tissue matrix material was 58.0±0.4° C. (N=5), and the value of enthalpy change was 61.6±2.1 Joule per gram by dry weight (N=5), which were not significantly different from the dermis matrix in natural state from the raw material of the dermis.

There was no significant change or damage on the characteristics of the dermis matrix in the whole process course.

Figure 2:
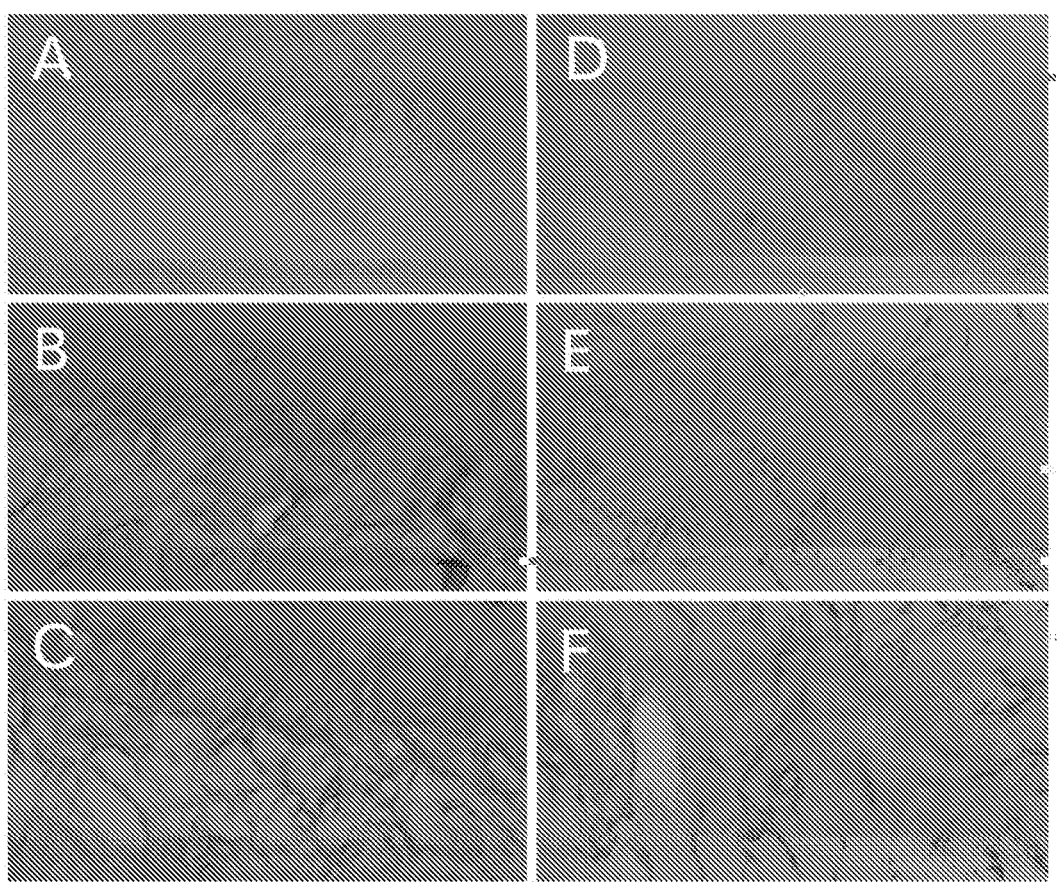
FIG. 2: Histology of tissue sections.
A, B, C: an immunochemical staining section of collagen type I;
D, E, F: an immunochemical staining section of collagen type III;
A, D: negative staining;
B, E: positive staining of an untreated fresh porcine dermis;
C, F: treated tissue dermal matrixes.

It was indicated by analysis of the tissue section that there were no cell components (e.g., deoxyribonucleic acid DNA) and α-1,3-galactose residue antigen in the matrix, see FIG. 1 for details. It was also showed by immunochemical staining analysis of collagen type I and III that there was no damage on the collagen in the dermis matrix in the treatment process, see FIG. 2 for details.

Example 2: Determination of Appropriate Conditions for Washing and Disinfecting the Dermis Fresh dermis was collected from a porcine body, and the fresh porcine dermis was treated in sodium hydroxide solutions with pH of 10.6, 11.5 and 11.8 at 37° C., respectively. Each kilogram of the porcine hide was in 4 litre of sodium hydroxide solution, with the control of phosphate buffer. After 24 hours, colony-forming unit per milliliter solution was determined. The phosphate buffer contained 10.3±1.3 logarithmic colony-forming unit (Log CFU)(N=3); and the logarithmic colony-forming unit in the solution with pH of 10.6, 11.5 and 11.8 was 2.1±0.1, 0 and 0, respectively. As could be seen, disinfection and sterilization effect in moderate alkaline solution was significant.

It was demonstrated by using differential scanning calorimeter that the tissue matrix was damaged by washing with an alkaline solution with a pH of 11.5 or more, and the stability of protein in the tissue matrix was significantly reduced. The damage of high pH on the tissue matrix further demonstrated the irreversible imbibition and induration of the tissue matrix. This example determined a more suitable condition for washing and disinfecting the dermis, which comprised adjusting pH to be between 10.5~11.5.

Example 3: Manufacture and Performance Detection of an Animal Acellular Tissue Matrix Material 1. Manufacture (1) Collection and Preservation of a Tissue and Organ
Fresh porcine hide was collected from a newly slaughtered pig, and temporarily preserved in a refrigerator at 4° C. After the porcine hide was dehaired mechanically, the porcine hide was split into a dermis layer having a thickness of about 1.0 mm.

(2) Collection and Washing
After collection and washing (see example 1), the porcine dermis with a thickness of 1.0 mm was temporarily preserved in a refrigerator at −80° C.

(3) Decellularization
After being thawed, the dermis was flushed with 5 mmol/L of hydroxyethylpiperazine ethane sulfonic acid solution (pH 7.4), and was then treated at 37° C. for 18 hours after adding 2.0 mmol/L of calcium chloride and 0.2 unit per milliliter of neutral dispase.

(4) Washing
The dermis was washed with 1.0% sodium deoxycholate solution at 37° C. for 20 hours.

(5) Digestion of DNA and α-1,3-Galactose Residue Antigen
After the dermis was flushed with sterile normal saline for 120 minutes, to each litre of the solution were further added 2.0 mM of calcium chloride, 2.0 mM of magnesium chloride, 4000 units of recombinant deoxyribonuclease and 200 GALU units of α-galactosidase extracted from seeds of green coffee bean, and the dermis was treated at 37° C. for 24 hours.

(6) Virus Inactivation
After being washed with sterile normal saline, the dermis was sterilized with 0.05% hydrogen peroxide, 0.30% acetic acid and 0.20% peroxyacetic acid for 2 hours.

(7) Washing
The dermis was flushed with a sterile normal saline until no sodium deoxycholate, recombinant deoxyribonuclease and α-galactosidase was remained.

(8) Terminal Sterilization Treatment
The treated dermal matrix was preserved in sterile normal saline solution containing 12% glycerin, and sterilized by 25 kGy of gamma ray.

2. Performance Detection

It was demonstrated by measurement using the durometer with OO-type probe that the softness of the untreated porcine dermis was 40±8.6 (N=24), the softness of the acellular porcine dermis was 13.0±4.0 (N=25), and the softness of human dermis was 14.2±6.1 (N=40). It was demonstrated that there was no statistically significant difference in the softness between the porcine dermal matrix after decellularization treatment and the human dermis tissue, as compared to the untreated porcine dermis (much harder). Further, it was demonstrated that the method of the examples of the present invention improved the flexibility, drapability and the integration performance of wound curved surface of the tissue matrix.

It was demonstrated by analysis of the tissue section that α-1,3-galactose residue antigen of the produced tissue matrix was removed completely, the result of staining was negative, and no antigen was expressed. DNA content was determined by using a QUANT-IT™-PICOGREEN™ fluorochrome method, the results of which indicated that each gram of the fresh porcine dermis contained about 84.0±10.2 microgram of DNA (N=3), each gram of the porcine dermis after being washed and disinfected contained 62.9±9.5 microgram of DNA (N=3), each gram of the tissue matrix after being treated by decellularization and washed only contained 1.9±1.1 microgram of DNA (N=3), and the animal DNA content was averagely reduced by 97.7%. It was showed by analysis using differential scanning calorimeter that the initial denaturation temperature of the tissue matrix material was 54.7±0.2° C. (N=3), the value of enthalpy change was 59.5±3.1 Joule per gram by dry weight (N=3). As compared with the dermis in natural state from the raw material of the porcine dermis, the initial denaturation temperature was only reduced by 3.3° C., and there was no significant difference in the value of enthalpy change, which illustrated that there was no significant change or damage on the characteristics of the tissue matrix in the whole manufacture process (including terminal radiation sterilization by gamma ray).

The content of collagen in the tissue matrix was determined by hydroxyproline method, and the tissue matrix of porcine hide after terminal radiation sterilization by gamma ray contained 91.0±3.0% (N=6) of collagen. The content of elastin was determined by FASTIN™ staining method, and the tissue matrix after terminal radiation sterilization by gamma ray contained 0.92±0.21% (N=6) of elastin, which was reduced by 71.4% as compared with the untreated porcine dermal material.

Figure 3:
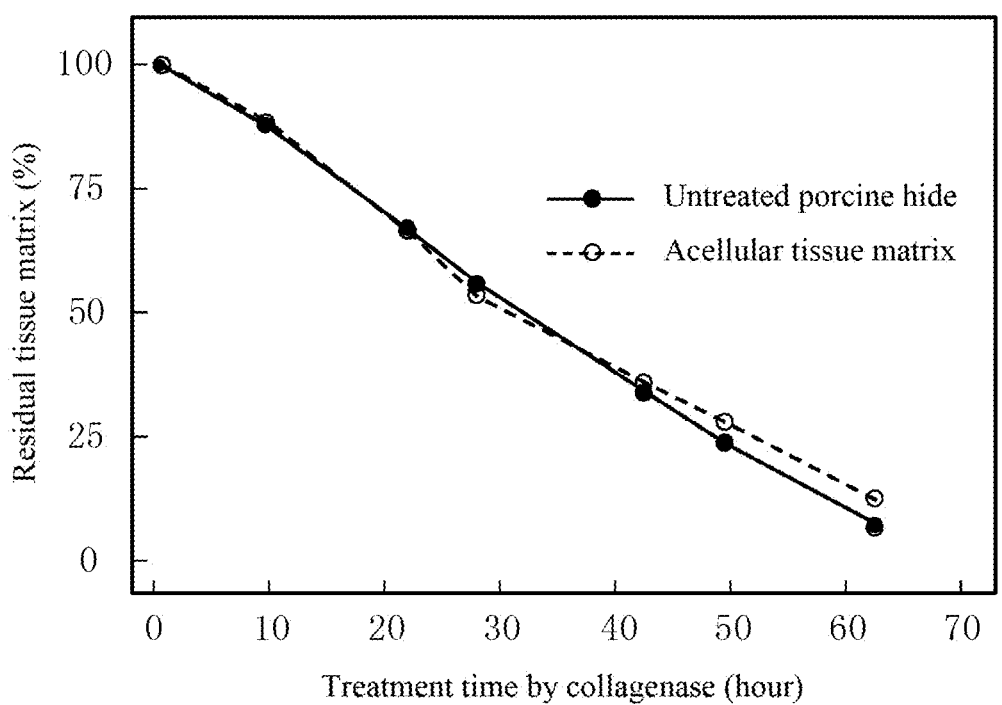
FIG. 3: A characteristic diagram of an acellular tissue matrix material against the hydrolysis via collagenase after the terminal sterilization by gamma ray irradiation.

Characteristics of the acellular tissue matrix material against hydrolysis via collagenase may be used to study the stability of collagen in the acellular tissue matrix material manufactured by the examples of the present invention after terminal radiation sterilization by gamma ray. The manufactured acellular tissue matrix material was placed into a trihydroxymethyl aminomethane-hydrochloric acid solution containing 5 units of collagenase per milliliter (10 mM, pH 7.5), and incubated at 37° C. for up to 64 hours. The results showed that as compared with the untreated porcine dermal material, characteristics of the acellular tissue matrix manufactured by the method of the examples of the present invention against hydrolysis via collagenase did not change after terminal radiation sterilization by gamma ray, see FIG. 3 for details.

Figure 4:
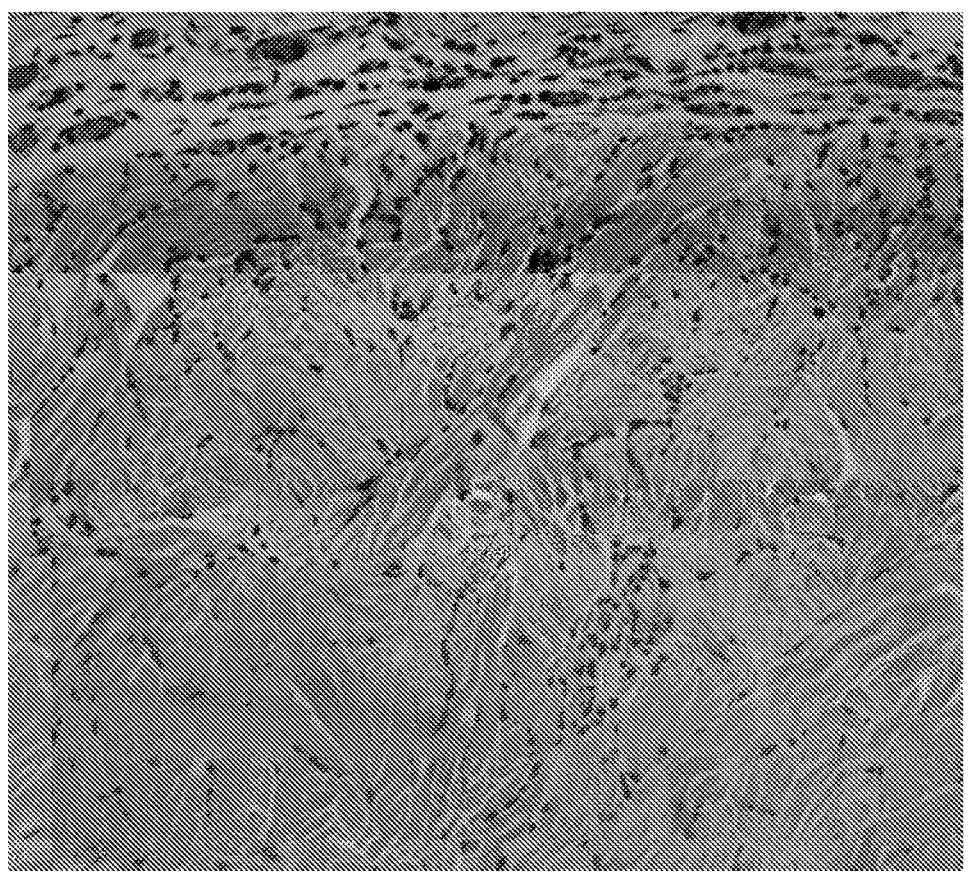
FIG. 4: An HE staining histology showing host cell ingrowth and neovascularization, after two weeks from the subcutaneous implantation of an acellular tissue matrix material into a rat.

By utilizing recellularization characteristics of the acellular tissue matrix material manufactured by the method of the examples of the present invention, an animal evaluation experiment was performed with rats (*Rattus norvegicus* Lewis). After 8 rats were narcotized, the hair on the back was removed off by an electrical shaver, the surgical site was scrubbed with 70% alcohol, and a separate incision was cut on the upper and lower and left and right back, to form a small pocket, the size of which was suitable to accommodate 1×1 cm of sample (about 1 mm thick). The acellular tissue matrix material sample was subcutaneously implanted into the rat. After the surgery, if the rats showed signs of pain, a buprenorphine solution (0.05 mg/kg) was used to stop pain. The rats were sacrificed after two weeks, and the implanted acellular tissue matrix material was taken out and fixed with a 10% neutral formalin solution. Host cell ingrowth and angiogenesis of rats were observed by a tissue section method. The results demonstrated that a large number of host cells were grown into the tissue matrix material within two weeks, and the neovascularization began, with no adverse reaction being observed, see FIG. 4 for details.

Example 4: Comparative Study for Two Tissue Process Methods of Making Acellular Tissue Matrices The following contents summarize the findings of the comparative study for two tissue process methods of making acellular tissue matrices.

The inventors of the present application have characterized the acellular tissue matrices derived from porcine skin material with the Gratzer method (WO 2011/132089 A2, D1) and the application method. The detailed description of these methods for processing skin material is shown in the following tables. The D1 method (WO 2011/132089 A2) is described in Table 1. The application method is described in Table 2, including three surfactant treatment variations (RJ-1, RJ-2 and RJ-3) to schematically show three parallel technical schemes of the present application.

TABLE 1

The process method of D1 (WO 2011/132089 A2, the D1 method)

| Steps | Process Description |
|---|---|
| 0 | collect the porcine skin material from three 5-6 month animals (replications), trim the skin material to the size of 4 × 5 cm and thickness of ~1.5 mm, store raw sample materials at a −25° C. freezer before tissue process. |
| 1 | Thaw the skin material at 20-25° C. |
| 2 | Contact the skin material with a hypotonic solution (10 mM Tris buffer containing 5 mM EDTA, 0.35 mL/L PMSF (P7626), 50000U penicillin/streptomycin in 300 mL solution, pH 8.0) for 24 hours with a solution change after 12 hours at 20-25° C. on a rotation shaker (40-65 rotations per min). The ratio of the process solution to tissue volume is 50:1. [This solution to tissue volume ratio was used in all process steps below.] |
| 3 | Contact the lysed skin tissue with a first surfactant solution (1% v/v Triton x100 containing 5M KCl, 5 mM EDTA, 50 mM Tris, 0.35 mL/L PMSF (P7626), 50000U penicillin/streptomycin in 300 mL solution, pH 8.0) for 36 hours with a solution change every 12 hours at 20-25° C. on a rotation shaker (40-65 rotations per min). |
| 4 | Rinse the surfactant-treated tissue material with 300 mL sterile deionized water. |
| 5 | Rinse in Hanks/HEPES buffer (0.14M NaCl, 5.4 mM KCl, 0.26 mM $Na_2HPO_4$, 0.44 mM $KH_2PO_4$, 4.2 mM $NaHCO_3$, 10 mM HEPES, 8.3 mM $CaCl_2 \cdot 2H_2O$, 0.2 mM $MgSO_4 \cdot 7H_2O$, 0.25 mM Mg $Cl_2 \cdot 6H_2O$, pH 7.35) for 30 min. |
| 6 | Contact the surfactant-treated tissue material with a nuclease enzyme solution (1330 μL RNase (R5125) stock solution and 1330 μL DNase (D4527) stock solution, 200 mL Hanks/HEPES solution) for 5 hours at 37° C. on a rotation shaker (45-60 rotations per min) |
| 7 | Contact the nuclease-treated tissue material with a cleaning solution comprising a second surfactant (1% TnBP in 50 mM Tris buffer (pH 9) containing 50000U penicillin/streptomycin in 300 mL solution for 30 hours with a solution change every 10 hours at 20-25° C. on a rotation shaker (40-65 rotations per min). |
| 8 | Rinse the TnBP-treated tissue material with 50 mM Tris buffer (pH 9) containing 50000U penicillin/streptomycin in 300 mL solution for 24 hours with a solution change every 12 hours at 20-25° C. on a rotation shaker (40-65 rotations per min). [Take samples for tissue matrix characterization.] |
| 9 | Contact the decellularized tissue with a bioburden reducing agent solution (2% PAA/100% ethanol/sterile water, at a volume ratio of 2/1/1) for 4 hours at 20-25° C. on a rotation shaker (40-65 rotations per min). |
| 10 | Rinse the processed tissue material with the PBS solution (0.14M NaCl, 2.7 mM KCl, 6.5 mM $Na_2HPO_4$, 1.5 mM $KH_2PO_4$, pH 7.4) containing 50000U penicillin/streptomycin in 300 mL solution for 12 hours at 20-25° C. on a rotation shaker (40-65 rotations per min). |
| 11 | Rinse the processed tissue material with PBS solution (0.14M NaCl, 2.7 mM KCl, 6.5 mM $Na_2HPO_4$, 1.5 mM $KH_2PO_4$, pH 7.4) for 30 min twice at 20-25° C. on a rotation shaker (40-65 rotations per min). |
| 12 | Terminal sterilization by 16-20 kGy gamma irradiation. [Take samples for tissue matrix characterization.] |

TABLE 2

The process method of the present application

| Steps | Process Description |
|---|---|
| 0 | collect the porcine skin material from three 5-6 month animals (replications), trim the skin material to the size of 4 × 5 cm and thickness of ~1.5 mm, store raw sample materials at a −25° C. freezer before tissue process. |
| 1 | Thaw the skin material in normal saline containing 100 mg/L gentamicin at a solution to tissue volume ratio = 4:1. [This solution to tissue volume ratio was used in all process steps below.] |
| 2 | Treat the skin material with an alkaline solution (2.5 mM NaOH, pH 11.4) for 24 hours at 20-25° C. on a rotation shaker (40-65 rotations per min). |
| 3 | Rinse the treated material with sterile water and adjust pH with acetic acid to neutral pH 6-8 range. |
| 4 | Rinse the neutralized material with saline (0.9%) solution containing 2 mM CaCl, 2 mM MgCl and 100 mg/L gentamicin for 1 hour. |
| 5 | Decellularize with 50 units/L dispase in 20 mM HEPES (pH 7.5) containing 2 mM CaCl and 2 mM MgCl at 37° C. for 24 hours on a rotation shaker (40-65 rotations per min). |
| 6/7 | RJ-1: Step 6: wash the dispase-treated material with 0.5% Triton x100 in 20 mM HEPES (pH 7.5) for 12 hours at 37° C. on a rotation shaker (40-65 rotations per min). Step 7: wash with 1.0% sodium deoxycholate in PBS solution (pH 7.5) for 24 hours at 20-25° C. on a rotation shaker (40-65 rotations per min). — RJ-2: Step 6: N/A. Step 7: wash the dispase-treated material with 1.0% sodium deoxycholate in PBS solution (pH 7.5) for 24 hours at 20-25° C. on a rotation shaker (40-65 rotations per min). — RJ-3: Step 6: wash the dispase-treated material with 0.5% Triton x100 in 20 mM HEPES (pH 7.5) for 12 hours at 37° C. on a rotation shaker (40-65 rotations per min). Step 7: N/A. |
| 8 | Rinse the decellularized material with 20 mM HEPES (pH 7.5) for 6 hours (solution change after 2 hour) at 20-25° C. on a rotation shaker (40-65 rotations per min). |
| 9 | Treat the decellularized material with 5000 enzyme units/L DNase in 100 mM Tris-HCL (pH 7.2) containing 2.0 mM $CaCl_2$, 2.0M $MgCl_2$ for 20 hours at 37° C. on a rotation shaker 40-65 rotations per min). |
| 10 | Rinse the DNase-treated material with saline for 2 hours (solution change after 1 hour) at 20-25° C. on a rotation shaker (40-65 rotations per min). |
| 11 | Treat the DNase-treated material with 400GALU units/L α-galactosidase prepared in 10 mM HEPES (pH 7.5) containing 2.0 mM $CaCl_2$, 2.0M $MgCl_2$ for 24 hours at 37° C. on a rotation shaker (40-65 rotations per min). |
| 12 | Wash the α-galactosidase-treated material with 3% NaCl for 4 hours (solution change after 2 hours) at 20-25° C. on a rotation shaker (40-65 rotations per min). [Take samples for tissue matrix characterization.] |
| 13 | Treat the processed tissue matrix for virus inactivation with 0.02% hydrogen perioxide, 0.15% acetic acid and 0.10% peroxyacetic acid for 2 hours at 20-25° C. on a rotation shaker (40-65 rotations per min). |
| 14 | Rinse the virus-inactivated material with the PBS solution (pH 7.5) for 6 hours (solution change after 2 hour) at 20-25° C. on a rotation shaker (40-65 rotations per min). |
| 15 | Soak the tissue matrix material in 6% glycerin saline for at least 3 hours and then package. |
| 16 | Terminal sterilization by 16-20 kGy gamma irradiation. [Take samples for tissue matrix characterization.] |

Test Methods Used to Characterize the Properties of Tissue Matrices

1. Gross Appearance and Pliability of Tissue Matrices a) Observation for Gross Appearance:

Take out tissue matrix samples from the containers or pouches, held the tissue piece with a pair forceps along the diagonal line by half, and let the tissue piece drape natural. Observe the change in tissue drapability and take photo for record.

b) Measurement of Tissue Pliability with a Durometer:

1) Turn on the power of the Check Line MSDD-3-A durometer (with the OO probe). Calibrate the durometer's hardness reading score with the silicone standard. Make sure the reading falls within 82.4±4.0 when the OO probe is installed.

2) Place a layer of plastic wrap onto a soft foam, lay flat the tissue matrix and fold the tissue matrix in the middle.

3) Press the OO probe on the top of tissue matrix and held steadily. Do not apply additional force to press the tissue matrix except for the durometer's own weight.

4) When the durometer's reading stabilizes, record the hardness score. Measure at two different spots for each tissue piece.

2. Histology (H&E and Masson's Trichrome) of Tissue Matrices a) Paraffin Processing of Tissue Matrix:

1) Cut the tissue matrix into strips, 0.5 cm*1 cm, rinse 2-3 times with 0.9% saline for 5 to 10 min each time.

2) Fix with 10% Formalin solution for at least 24 hours.

3) Rinse the specimen with the phosphate-buffered solution (PH7.4) for 1-2 hours, change solution twice before dehydration.
4) Transfer the specimens sequentially from 70% ethanol to higher concentrations (80%, 90%, 95%, and 100% (I) and 100% (II)) for dehydration. Equilibrate for 30 min at each step.
5) Replace ethanol with xylol.
6) Infiltrate with wax and then embed the specimen into wax blocks according to the routine histological procedures.

b) H&E Staining:
1) Sectioned the specimens with a microtome to 5 μm thick.
2) Place tissue slices onto glass slide, remove was by reversing the steps from xylol to 70% ethanol. Then rinse out ethanol.
3) Stain the slices with hematoxylin and eosin respectively.
4) Seal the slice.

c) Masson Trichrome:
1) Sectioned the specimens with a microtome to 5 μm thick.
2) Place tissue slices onto glass slide, remove was by reversing the steps from xylol to 70% ethanol. Then rinse out ethanol.
3) Stain with Ponceau acid fuchsin for 2 min.
4) Seal the slice.

3. SEM Ultra-Structure of Tissue Matrices a) Sample Preparation:
1) Rinse 2-3 times with 0.9% saline for 5 to 10 min each time.
2) Cut the tissue matrix into proper sizes, 0.5 cm*0.5 cm.
3) Place back into plastic tube for rehydration in saline.

b) Sample Fixation:
1) Discard saline, and add 2% glutaraldehyde for 2-3 hours,
2) change to 4% glutaraldehyde and let for at least 24 hours.
3) Discard glutaraldehyde solution, rinse with phosphate-buffered saline twice.

c) Sample Dehydration and SEM Observation:
1) Discard phosphate-buffered saline
2) Add 50% ethanol for treatment (30 min).
3) Transfer the specimens sequentially to 70%, 80%, 95% (I), 95% (II), and 100% (I) and 100% (II) and 100% (III) for dehydration. Equilibrate for 30 min at each step.
4) Replace 100% ethanol with hexamethyl disilazane (HMDS): ethanol:HMDS at 1:2 (v/v) for 30 min, ethanol:HMDS at 2:1 (v/v) for 30 min, 100% HMDS (I), and 100% HMDS(II).
5) Allow HMDS to evaporate.
6) Gold sputtering and observation.

4. The Detection of aGal Epitopes (Immune-Histology)
1) Rinse samples with saline for 2-3 time, 5-10 min each.
2) Cut the specimen into 0.5 cm*1cm strips.
3) Place sample strips into 20% sucrose solution for at least 24 hours before sectioning.
4) Cryo microsection at −18 C.
5) Fixation in acetone at −20 C for 3 min.
6) Rinse with phosphate-buffered saline for 5 min.
7) Incubate with 3% hydrogen peroxide for 4 min.
8) Rinse with phosphate-buffered saline for 5 min, 3 times.
9) Incubate with 1% BSA for 1 h.
10) Add GSL I-B4 (vector B-1205) (1:50 dilution), and allow for 1-h incubation.
11) Rinse with phosphate-buffered saline for 5 min, 3 times
12) Add HRP (zymed 43-4323) (1:250 dilution), and allow for 30-min incubation/
13) Rinse with phosphate-buffered saline for 5 min, 3 times.
14) Color formation with DAB (MBI1241).
15) Observation.

5. Thermal Stability of Tissue Matrices
1) Cut samples into 4-5 mm in size, weigh about 15-25 mg.
2) Rinse with phosphate-buffered saline for 2-3 time
3) Weigh a pair of crucibles and record weight.
4) Remove surface water of tissue sample, place into crucibles and seal.
5) Weigh again to record tissue sample weight.
6) Scan the sample at 3° C./min from 10 C to 120 C under nitrogen gas purge (200 mL/min).
7) Drying sample. Punch a hole on the top of sealed crucibles and place into a oven at 100-110° C. for drying at least 5 h to get sample dry weight.
8) Data analysis: determine the onset temperature and melting enthalpy.

6. Determination of Collagen Content
1) Weigh ~20 mg dry sample into test tube.
2) Digest sample in glass tube with 3 mL 6N HCl for 5-7.5 h.
3) Take 0.15 mL sample solution. Top up with distilled water to 2 mL.
4) Prepare 2 mL microfuge tubes.
5) Add 50 μL diluted sample solution, add 100 μL isopropyl alcohol and 50 μL oxidation buffer, mix well and let react for at least 20 min.
6) Add 1.2 mL Erlich's reagent, mix well and incubate for 25 min at 60 C.
7) Cool down and read absorbance at 560 nm.
8) Standard curve
① Prepare 9 microfuge tubes, labeled from 1 to 9 as shown below.

| Tube # | Standard concentration (μg/mL) | Hydroxyproline (μL) | Distilled water (μL) |
|---|---|---|---|
| #1 | 80 | 1000 | 0 |
| #2 | 70 | 875 | 125 |
| #3 | 60 | 750 | 250 |
| #4 | 50 | 625 | 375 |
| #5 | 40 | 500 | 500 |
| #6 | 30 | 375 | 625 |
| #7 | 20 | 250 | 750 |
| #8 | 10 | 125 | 875 |
| #9 | 0 | 0 | 1000 |

② Prepare a new set of 9 microfuge tubes, labeled from 1 to 9 as shown above.
③ Add 50 μL standard sample solution, add 100 μL isopropyl alcohol and 50 μL oxidation buffer, mix well and let react for at least 20 min.
④ Add 1.2 mL Erlich's reagent, mix well and incubate for 25 min at 60 C.
⑤ Cool down and read absorbance at 560 nm.
9) Calculation of hydroxyl proline content in tissue matrix according to the standard curve.
10) Collagen content in tissue matrix=$\{2 \div 0.15 \times C \times 3 \div 12.5\% \div [1000 \times W \times (1-\omega)]\} \times 100\% = \{0.32 \ C \div [W \times (1-\omega)]\} \times 100\%$ where: C, hydroxyl proline content; W, sample weight, w, sample's water content; factor (2/0.15), dilution factor; 3, HCl volume; 12.5, hydroxyl proline content in collagen.

7. Determination of Elastin Content
1) Sample preparation: weigh ~30 mg dry sample, record the sample weight.
2) Place into 2 mL microfuge tubes.
3) Defat with acetone: ① add 300 μL acetone for 1-3 h extraction, ② replace with fresh acetone, ③ discard acetone, let residual acetone to evaporate.
4) Add 1 mL 0.25 M oxalic acid, and incubate at 100° C. for 1 hour,
5) Cool down and centrifuge at 5000 rpm for 10 min.
6) Collect supernatant into 5 mL tube.
7) Add 1 mL 0.25 M oxalic acid for the second incubation,
8) Cool down and centrifuge at 5000 rpm for 10 min.
9) Collect supernatant into 5 mL tube, and combine with the first extraction solution,
10) Prepare for solution test:
   ① For samples, label 1.5 mL microfuge tube, and add 100 μL sample solution.
   ② For blank samples, label twos 1.5 mL microfuge tube, add 50 μL 0.25 M oxalic acid
   ③ For a-elastin standard sample curves

| Standard sample # | 1 | 2 | 3 | 4 | 5 | 6 |
|---|---|---|---|---|---|---|
| α-elastin/μg | 12.5 | 12.5 | 25 | 25 | 50 | 50 |
| (1 mg/mL)volume/μL | 12.5 | 12.5 | 25 | 25 | 50 | 50 |
| 0.25M oxalic acid/μL | 37.5 | 37.5 | 25 | 25 | 0 | 0 |

11) α-elastin test:
   ① add 50 μL Elastin Precipitating Reagent, mix and wait for 10 min to precipitate elastin.
   ② Centrifuge for 10 min at maximum speed, and discard supernatant.
   ③ Invert tube and use paper to absorb liquid.
   ④ Add 0.5 mL Dye Reagent, resuspend the precipitate, and react for 2 hours.
   ⑤ Centrifuge for 10 min at maximum speed, and discard supernatant.
   ⑥ Invert tube and use paper to absorb liquid.
   ⑦ Add 125 μL Dye Dissociation Reagent and vortex to release the dye
   ⑧ Transfer solution to the 96-well plate and read at 513 nm.
   ⑨ Elastin content (%)=30We÷[W×(1−ω)×1000]100%
where We, elastin content in 100 μL sample solution; W, sample weight; w, sample water content; 30, dilution factor.

8. Determination of Saccharide Content
1) Label two sets of 2 mL microfuge tube, including two tubes for every samples (duplicates) and two tubes for control samples.
2) Weigh ~20 mg dry tissue sample and record sample weight.
3) Add 1 mL 10 mM Tris-HCl buffer (pH 7.5) and incubated at 75° C. for 20 min.
4) Cool down sample, and add 50 μL protease K solution (10 mg/mL). Incubate at 65° C. for digestion.
5) After 2 hours, shake tubes for aiding digestion
6) After complete digestion, add 10 mM Tris-HCl buffer and mix.
7) Label one set of 15 mL centrifuge tubes, and for each tube, add 1 mL sample solution.
8) Add 1 mL 5% phenol solution into sample tubes, mix
9) Add 5 mL concentrated Sulfuric acid, mix gently.
10) Cool down for one hour.
11) Read the absorbance at 485 nm. Use control sample (no glucose added) to set zero reading and as a reference for samples.
12) Standard curve preparation:
   ① add 0, 50, 100, 150 or 200 μg glucose into different tubes
   ② Add 1 mL 5% phenol and mix
   ③ Add 5 mL concentrated sulfuric acid and mix gently.
   ④ Cool down and read the absorbance at 485 nm.
13) saccharide content: =2C÷[W×(1−ω)×1000]×100%
where C, glucose content corresponding to the absorbance reading in the standard curve; W, sample mass; ω, sample water content.

9. The Resistance of Tissue Matrices to Collagenase
1) cut tissue into pieces weighing 3-5 mg, and place 25-30 mg into each tube.
2) Add 1.5 ml to rehydrate for 1-2 h, rinse twice (20-30 min each time).
3) Discard solution, and remove all liquid.
4) Add 1.5 ml Tris-HCl working solution.
5) Take the first tube as control without adding collagenase working solution.
6) For the rest samples, add 30 ul collagenase working solution to a final enzyme concentration of 20 U/ml.
7) Mix and incubate at 37° C. for 8, 16, 24, 36, 48, 60 or 72 h.
8) Centrifuge and discard supernatant.
9) Add 1.5 ml distilled water to resuspend pellet. Centrifuge again and discard supernatant
10) Freeze dry the sample.
11) Weigh sample remaining and calculate the % loss of tissue mass after incubation.

10. The Resistance of Tissue Matrices to Trypsin
1) cut tissue into pieces weighing 3-5 mg, and place 25-30 mg into each tube.
2) Add 1.5 ml to rehydrate for 1-2 h, rinse twice (20-30 min each time).
3) Discard solution and remove all liquid.
4) Add 1.4 ml Tris-HCl working solution containing 2 mM $CaCl_2$ and add 100 uL trypsin solution (10 mg/mL).
5) Incubate at 37° C. for 72 h. After 72 h, centrifuge at 12000 rpm for 5 min.
6) Discard supernatant and add 1.5 mL distilled water to resuspend the pellet. Centrifuge again and discard the supernatant,
7) Freeze dry sample
8) Weigh the tissue weight.
9) Calculate the % weight loss of samples.

11. Tensile Test
1) Cut sample into precise 1 cm×5 cm strip. For each tissue piece (4×5 cm), cut two strips.
2) Place samples into phosphate buffered saline or 0.9% saline.
3) Set Instron extension speed at 150 mm/min and gap length at 40 mm.
4) Grip the sample, set zero and start testing.
5) Calculate maximum break strength (load), breaking extension (strain), extension at 5N (strain) and the Young's modulus.

As recited above, this study used porcine skin material from three animals at the age of 5 to 6 months. Skin material from each animal was collected, trimmed and labeled separately, using as three experimental replications. Collected materials were stored at a −25° C. freezer before use. Skin pieces of each animal were randomly distributed into each of four groups (D1, RJ-1, RJ-2 and RJ-3) for further processing according to the D1, RJ-1, RJ-2 and RJ-3 protocols, respectively.

Samples of acellular tissue matrices were taken for testing at two different process stages. The first batch of samples was taken after the completion of decellularization and washing (i.e., after Step #8 for the D1 protocol, and after Step #12 for RJ-1, RJ-2 and RJ-3 protocols). The samples taken immediately after decellularization and wash were tested for their gross appearance, pliability, the presence of aGal epitopes (immune-histology), tissue histology (HE, Masson's trichrome), ultra-structure and thermal stability. The second batch of samples was taken after terminal sterilization (i.e., after Step #12 for the D1 protocol, and after Step #16 for RJ-1, RJ-2 and RJ-3 protocols). Samples taken after terminal sterilization were tested for their gross appearance, pliability, tissue histology (HE, Masson's trichrome), ultra-structure, thermal stability, tensile strength, collagen content, elastin content and saccharide content, as well as the resistance to collagenase and trypsin digestion. The description of test methods used in this study is as recited above.

Results

1. Gross Appearance and Pliability of Tissue Matrices

Figure 5:
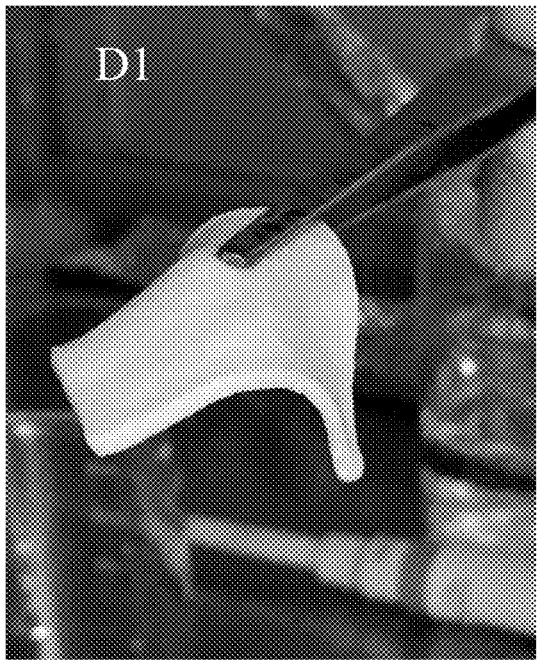
FIG. 5: Gross appearance of decellularized tissue matrices derived from porcine dermis by the Methods of D1 and the Application. Tissue matrices produced by the D1 method was rigid and stiffer than those produced by any of three treatment variations in the Application method (RJ-1, RJ-2 and RJ-3).
Figure 5:
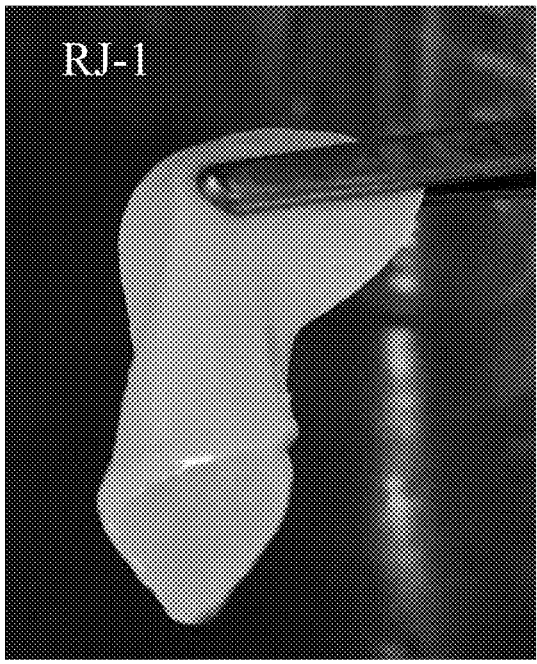
Figure 5:
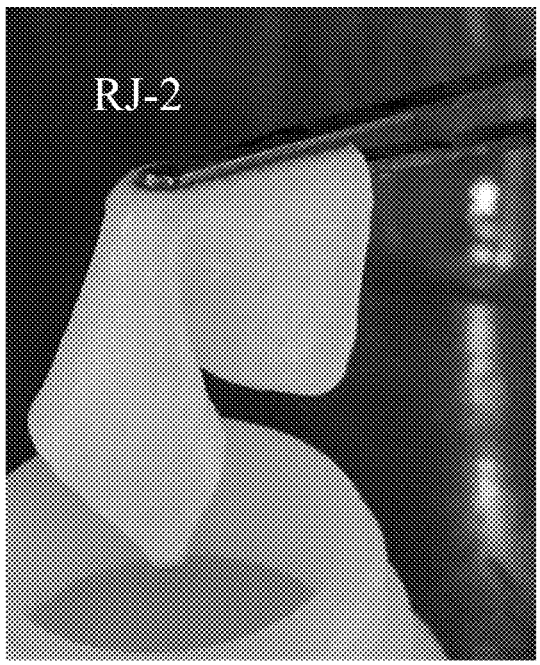
Figure 5:
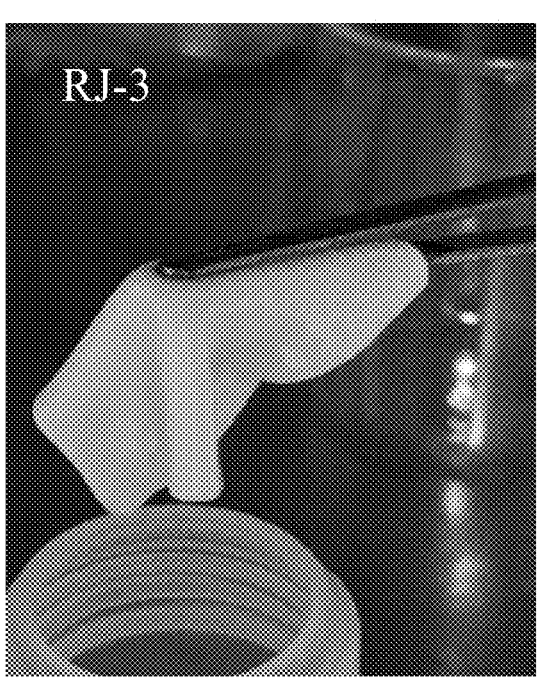
Figure 6:
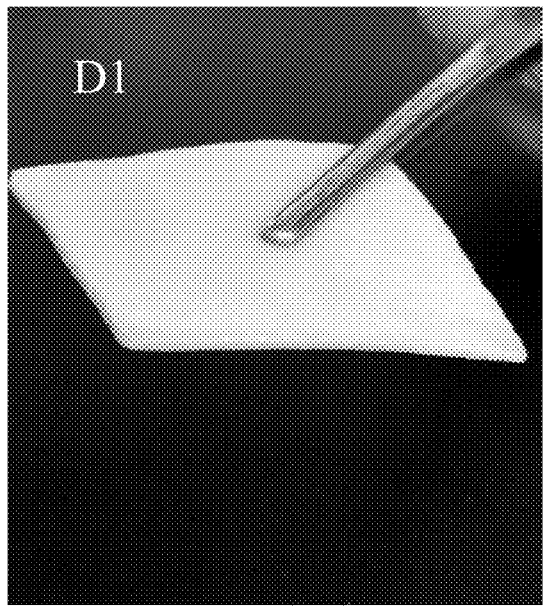
FIG. 6: Gross appearance of terminally-sterilized tissue matrices derived from porcine dermis by the Methods of D1 and the Application. Gamma irradiation increases the tissue stiffness.
Figure 6:
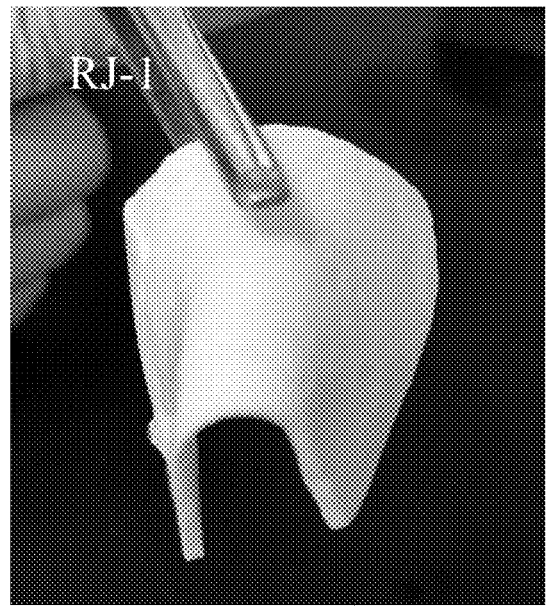
Figure 6:
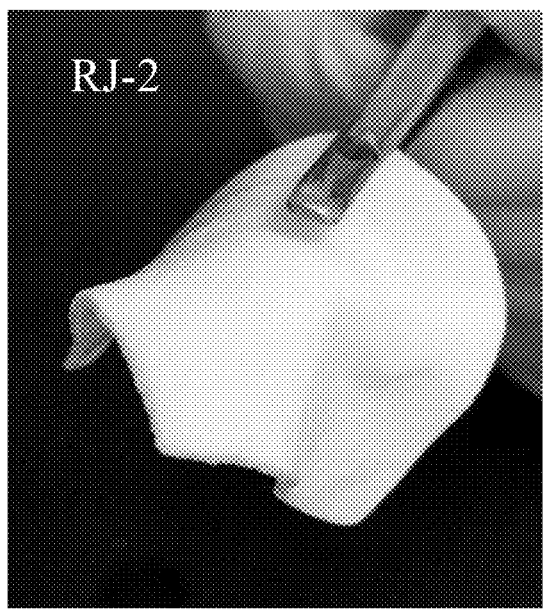
Figure 6:
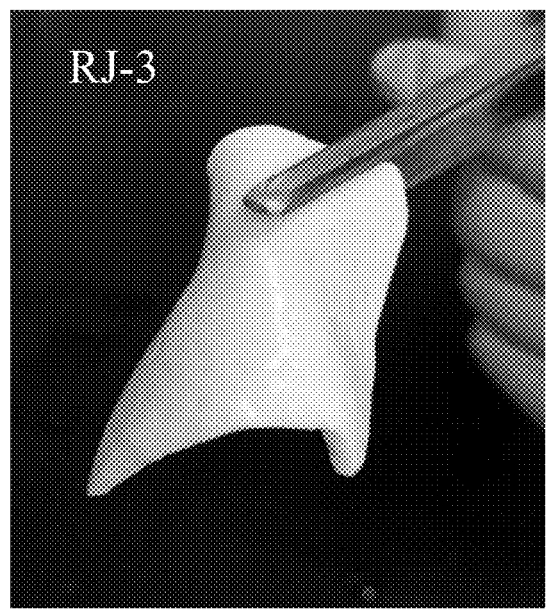

Tissue matrices produced by the method of D1 was more rigid and stiffer than those produced by any of three treatment variations in the Application. The difference in the pliability of tissue matrices was noticeable as early as in the process step #6 in the D1 protocol. FIG. 5 and FIG. 6 compare the gross appearance of decellularized tissue samples and terminally-sterilized tissue samples produced by the D1, RJ-1, RJ-2 and RJ-3 protocols, respectively. It shows the poor drapability of tissue matrices produced by the D1 protocol, as opposed to the softness of tissue matrices produced by any of the three variations (RJ-1, RJ-2 or RJ-3) in the Application method.

To compare the process-induced changes in the pliability of tissue matrices, we used Check Line MSDD-3-A durometer with the OO probe to measure the shore hardness score of tissue matrices. The test result is presented in Table 3. The hardness score is 27.4±4.1 for unprocessed porcine skin, which also contains epidermis and cells (N=9). Decellularized tissue matrices from the D1 method has the same hardness score as unprocessed porcine skin does, whereas decellularized tissue matrices from the RJ-1, RH-2 and RJ-3 methods in the Application are significant softer than unprocessed porcine skin and the D1 tissue matrices. After terminal sterilization by gamma irradiation, the hardness score of decellularized tissue matrices from the D1 method increases to 46.3±7.0, whereas the hardness score of decellularized tissue matrices from the RJ-1, RJ-2 and RJ-3 methods are still significantly lower than unprocessed porcine skin, less than half of the value of the D1 tissue matrices.

Therefore, the gross appearance, drapability and pliability of tissue matrices produced by the D1 method and the Application method are quite different.

TABLE 3

The pliability scores of tissue matrices made with different methods

| Method | Decellularized tissue matrices | Terminally sterilized tissue matrices |
|---|---|---|
| D1 | 27.4 ± 5.9 | 46.3 ± 7.0 |
| RJ-1 | 8.9 ± 3.6 | 16.2 ± 6.2 |
| RJ-2 | 14.7 ± 1.8 | 20.5 ± 2.8 |
| RJ-3 | 14.7 ± 3.9 | 16.3 ± 3.1 |

\* The values are the mean ± standard deviation.
N = 3 and 9 for the decellularized sample batch and the terminally-sterilized sample batches, respectively.

2. Histology (H&E and Masson's Trichrome) of Tissue Matrices

Figure 7:
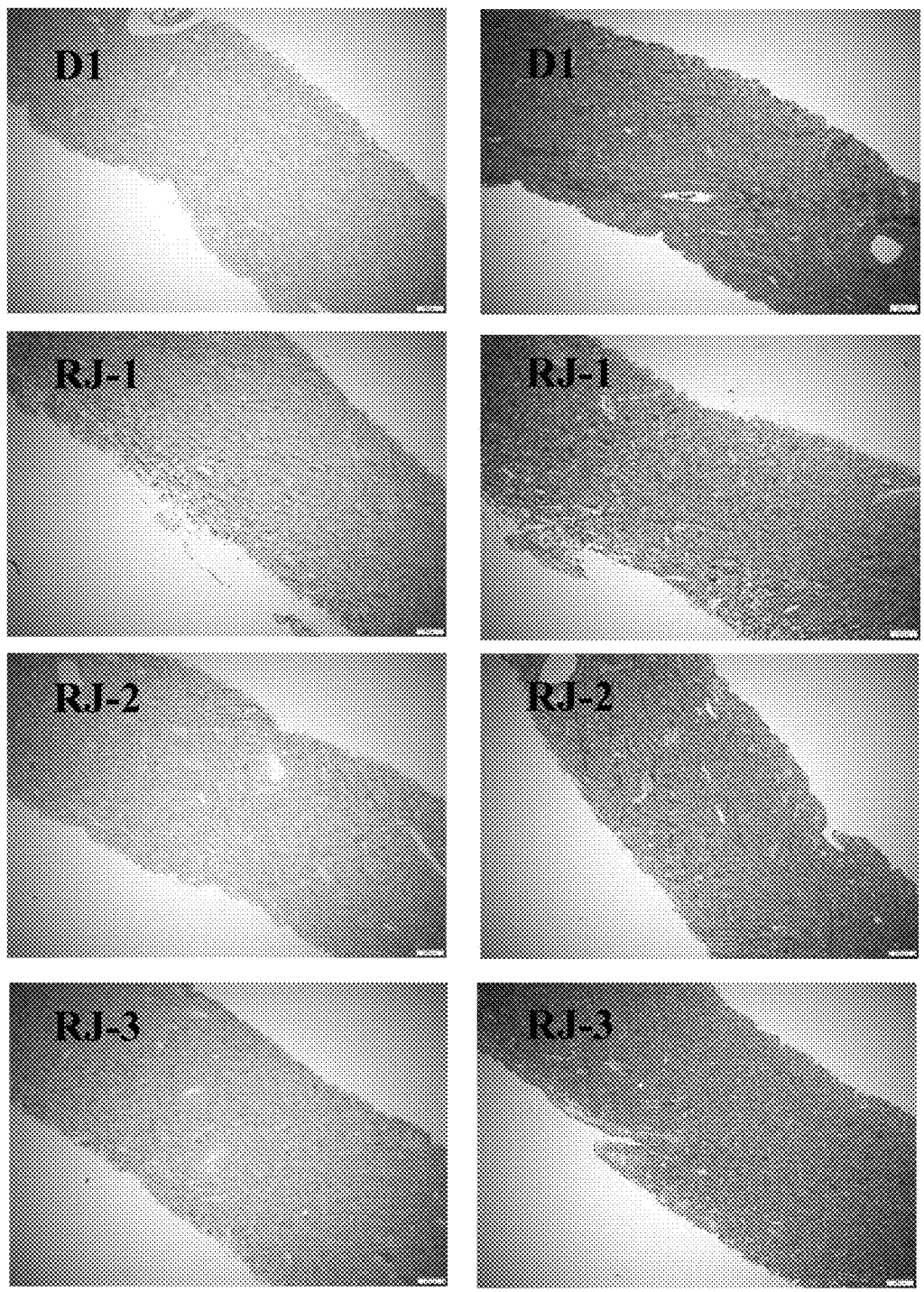
FIG. 7: Typical histological micrographs of H&E and Masson Trichrome stains of decellularized tissue matrices derived from porcine dermis by the Methods of D1 and the Application.
Figure 8:
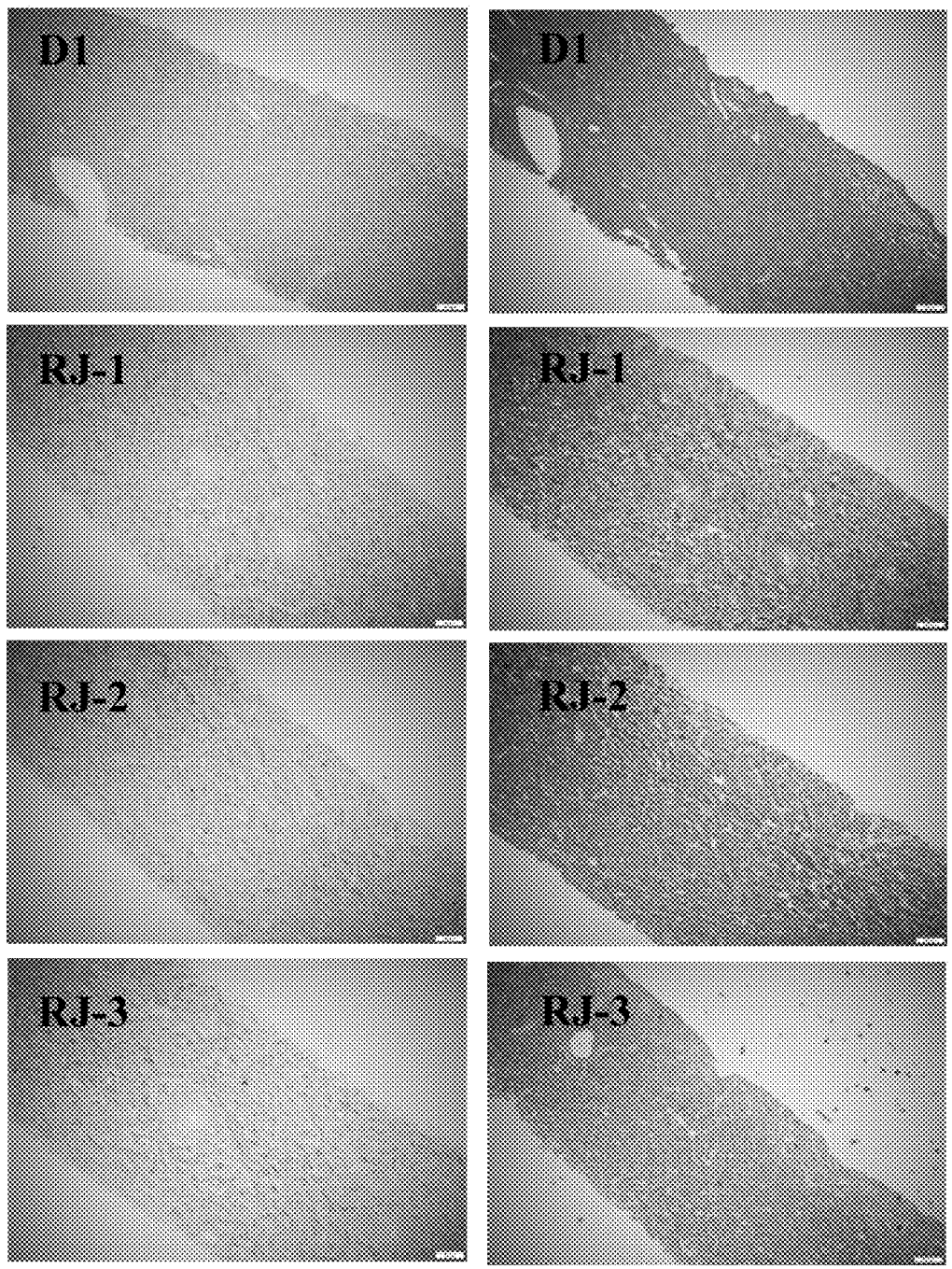
FIG. 8: Typical histological micrographs (40×) of H&E and Masson Trichrome stains of terminally-sterilized tissue matrices derived from porcine dermis by the Methods of D1 and the Application.
Figure 9:
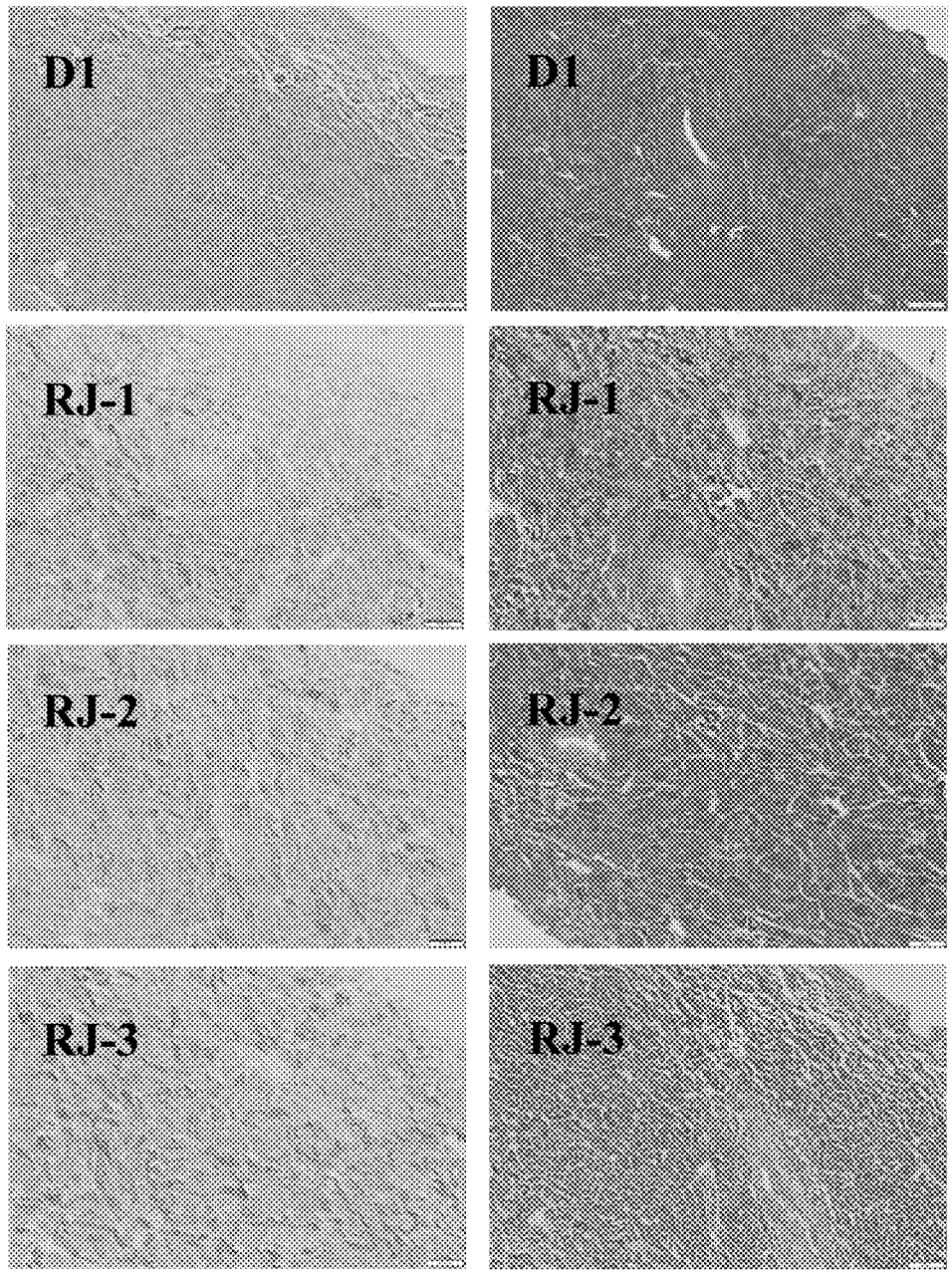
FIG. 9: Typical histological micrographs (100×) of H&E and Masson Trichrome stains of terminally-sterilized tissue matrices derived from porcine dermis by the Methods of D1 and the Application.

FIG. 7, FIG. 8 and FIG. 9 compare the histological micrographs of decellularized tissue samples and terminally-sterilized tissue samples produced by the D1, RJ-1, RJ-2 and RJ-3 of the Application protocols, respectively. H&E staining and Masson's Trichrome straining of decellularized tissue samples show only slightly denser in the D1 samples than in the RJ-1, RJ-2 and RJ-3 samples (FIG. 7), but after terminal sterilization H&E staining and Masson's Trichrome straining both show significantly denser in the D1 samples than in the RJ-1, RJ-2 and RJ-3 samples of the Application (FIG. 8 and FIG. 9). Collagen fibers in the D1 samples are packed more tightly, whereas collagen fibers in the RJ-1, RJ-2 and RJ-3 samples of the Application are much better separated.

3. SEM Ultra-Structure of Tissue Matrices

Figure 10:
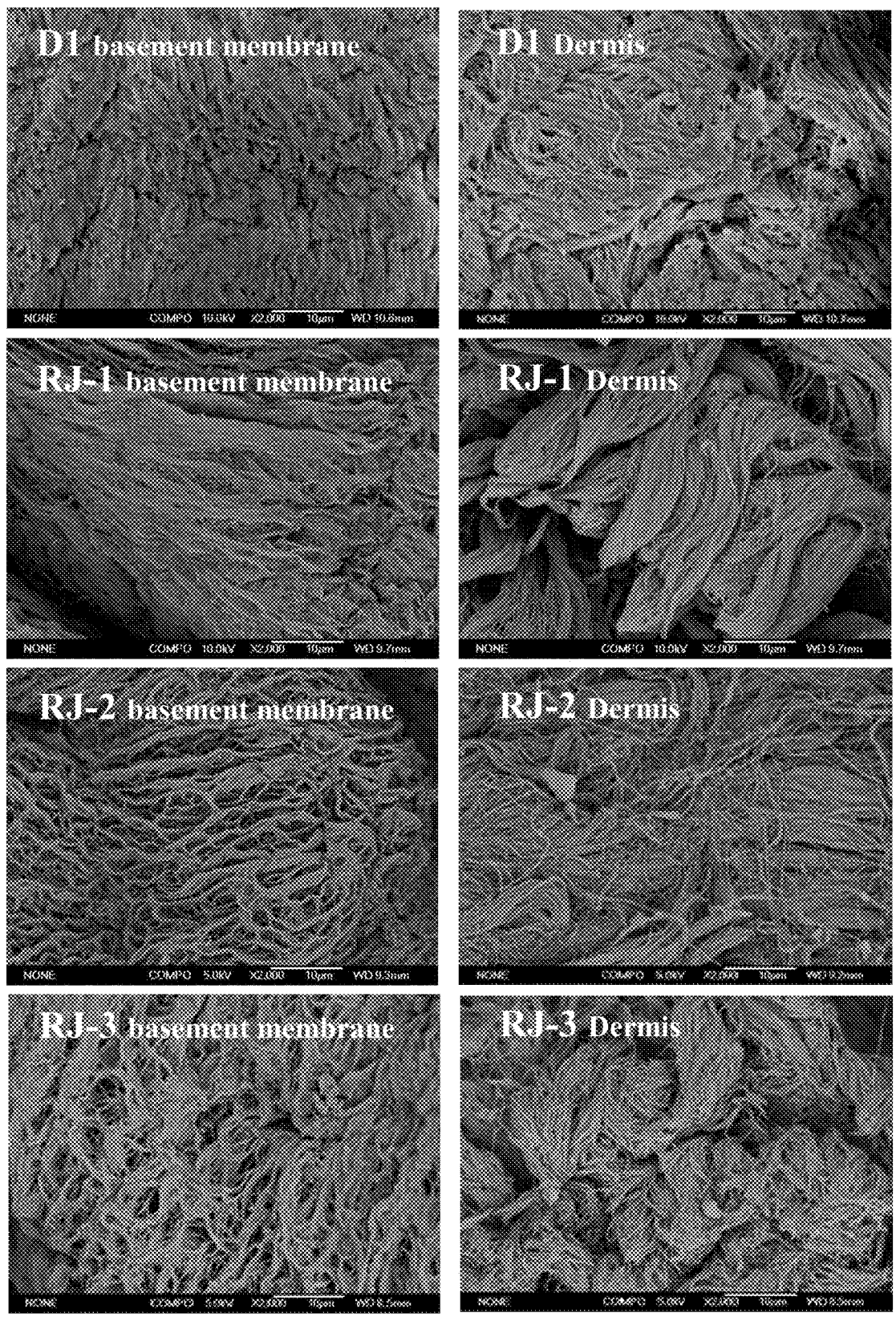
FIG. 10: SEM micrographs (2000×) of decellularized tissue matrices derived from porcine dermis by the Methods of D1 and the Application.
Figure 11:
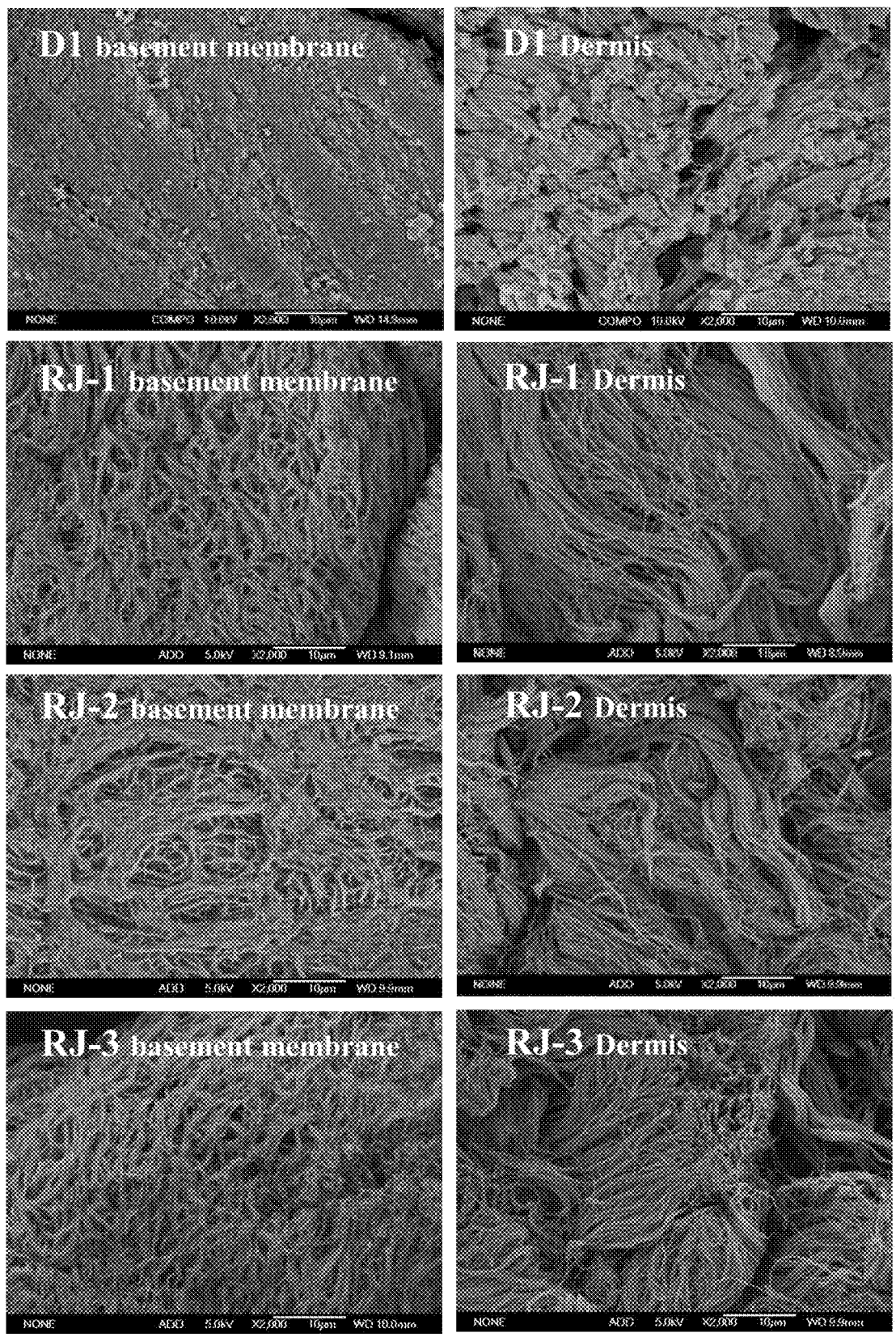
FIG. 11: SEM micrographs (2000×) of terminally-sterilized tissue matrices derived from porcine dermis by the Methods of D1 and the Application.

FIG. 10 and FIG. 11 compare the SEM ultra-structure of decellularized tissue samples and terminally-sterilized tissue samples produced by the D1, RJ-1, RJ-2 and RJ-3 of the Application protocols, respectively. The fibril structure is much less well-defined in the D1 samples than in the RJ-1, RJ-2 and RJ-3 samples of the Application, and there exist non-structural gel-like substances between collagen fibrils. The observation is consistent with the above-mentioned histological findings that tissue matrices made with the D1 method has lower porosity than those made with the Application method.

4. The Presence of αGal Epitopes (Immune-Histology)

Figure 12:
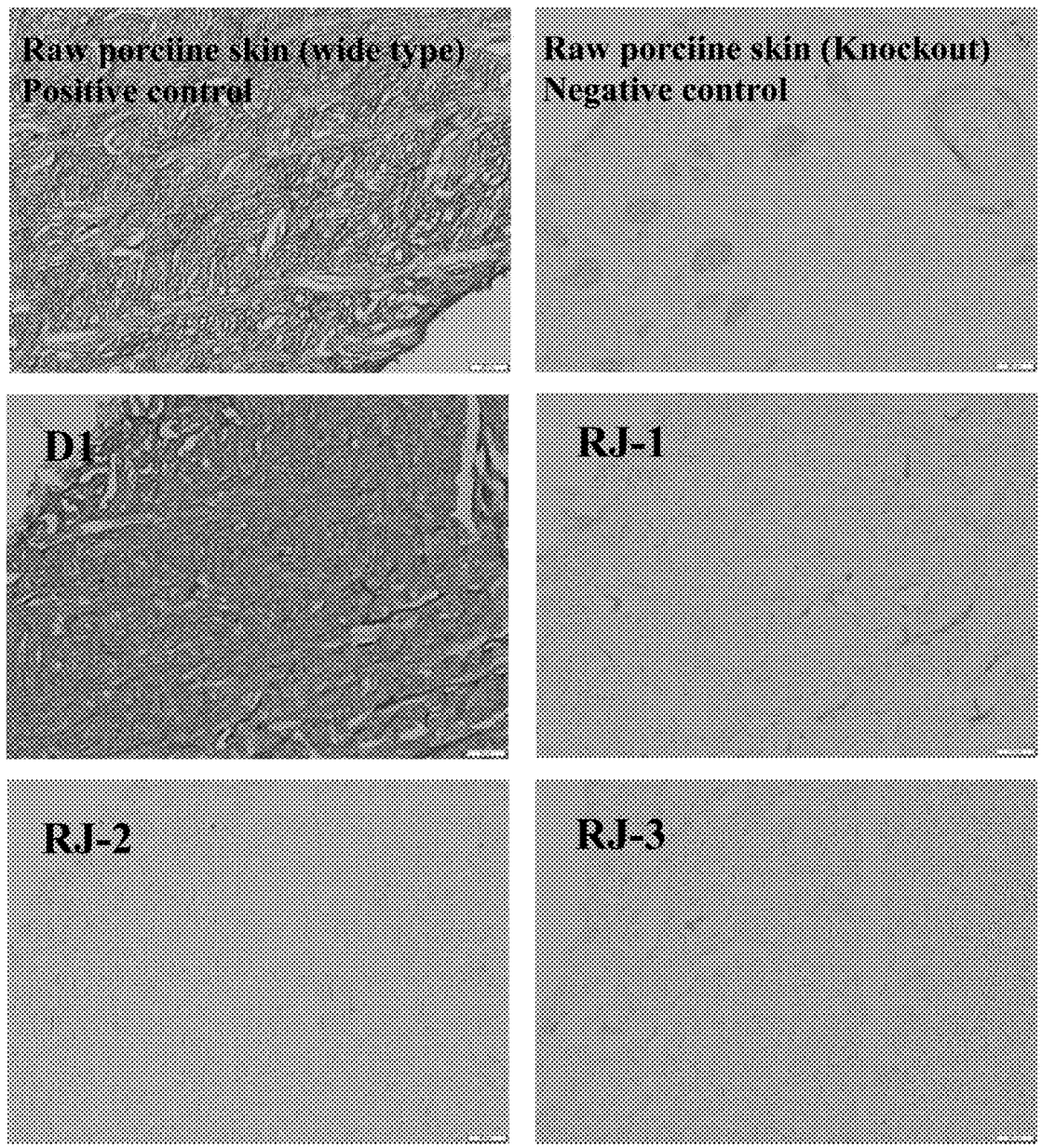
FIG. 12: Immunohistology of (100×) decellularized tissue matrices derived from porcine dermis by the Methods of D1 and the Application.

The presence of aGal antigen is the major barrier for cross species implantation. FIG. 12 shows the positive staining with Lectin I isolectin B4 in the decellularized tissue matrices made with the D1 method, showing the presence of αGal epitopes (antigen). The staining intensity in the D1 samples is comparable to the untreated porcine skin, demonstrating that the D1 method has no effect in reducing the matrix-bound αGal antigen. In contrast, the samples produced by any of the three protocols (RJ-1, RJ-2 and RJ-3) disclosed in the Application method are negative with Lectin I isolectin B4.

5. Thermal Stability of Tissue Matrices

Figure 13:
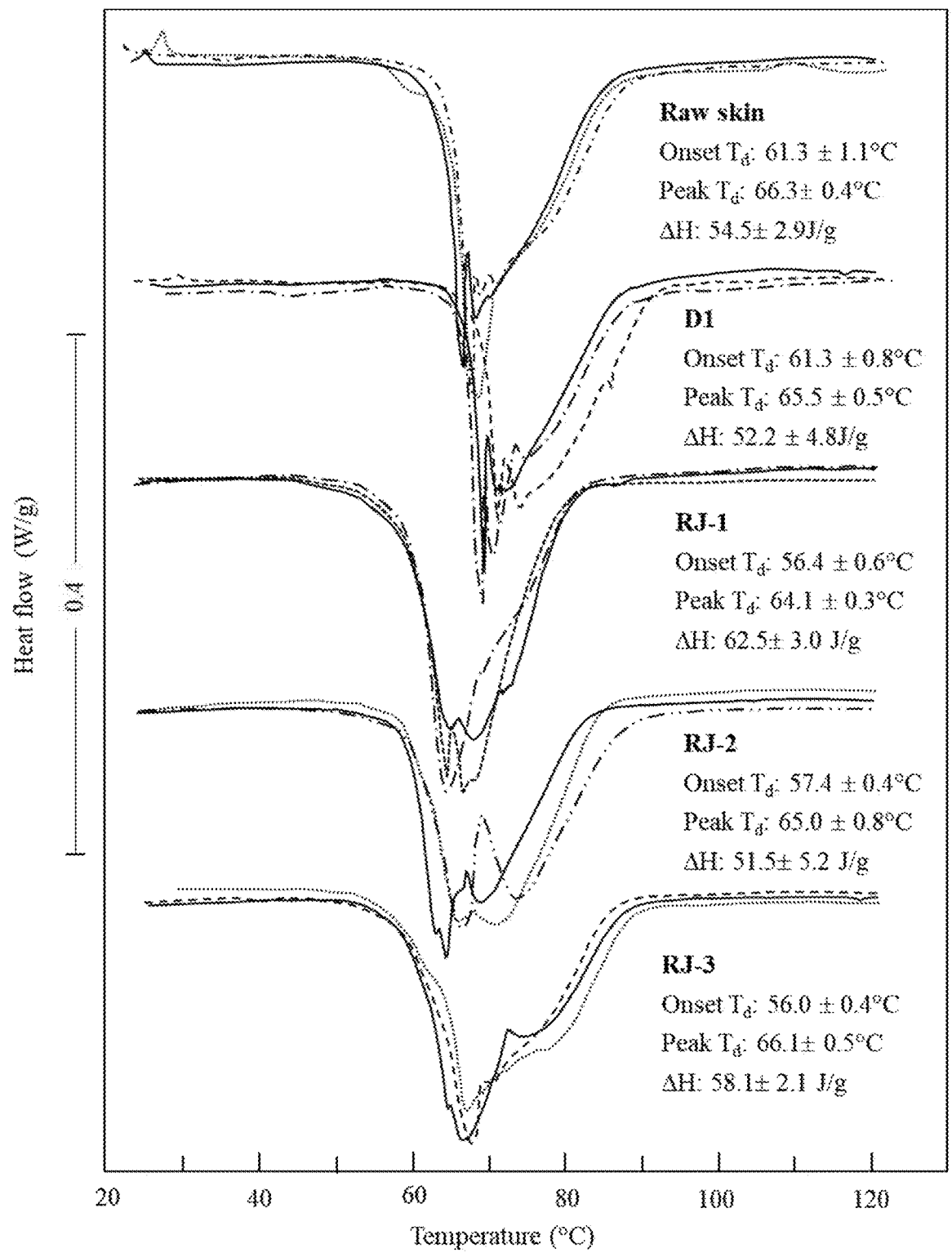
FIG. 13: calorimetric thermograms of decellularized tissue matrices derived from porcine dermis by the Methods of D1 and the Application.

FIG. 13 compare the thermal stability of decellularized tissue samples produced by the D1, RJ-1, RJ-2 and RJ-3 of the Application protocols, respectively. In comparison to the raw porcine skin material, the decellularization process steps of the D1 method do not alter the thermal stability profile as illustrated by the onset or peak denaturation temperature ($T_d$), the enthalpy of protein denaturation, as well as the shape of thermograms. The decellularization process steps of the Application method depress the onset denaturation temperature ($T_d$) by 4 to 5° C., a value that represents a significant shift.

Figure 14:
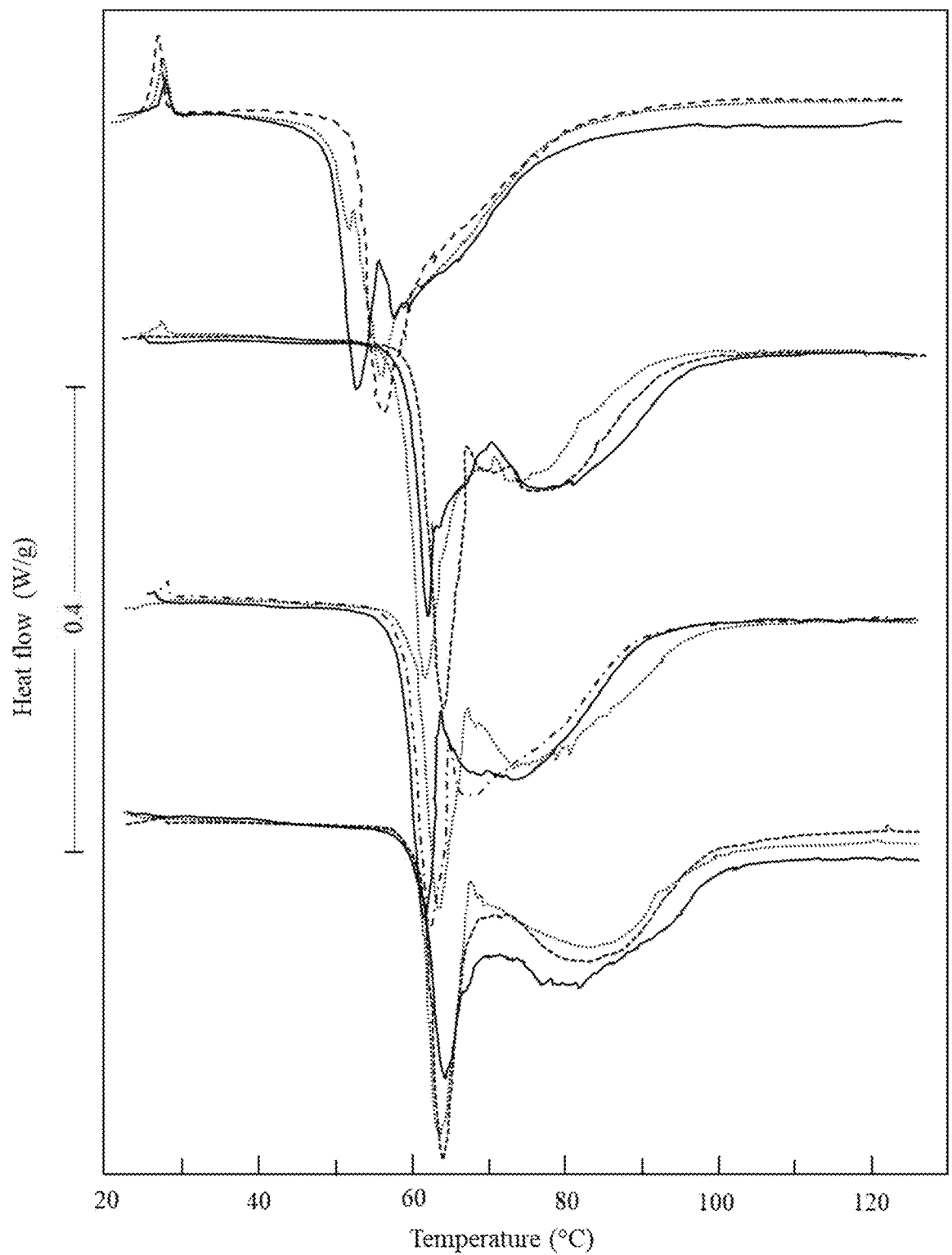
FIG. 14: calorimetric thermograms of terminally-sterilized tissue matrices derived from porcine dermis by the Methods of D1 and the Application. From the top to the bottom: D1, RJ-1. RJ-2 and RJ-3

However, more striking differences were detected in terminally-sterilized tissue samples produced by the D1, RJ-1, RJ-2 and RJ-3 of the Application protocols (FIG. 14). Upon gamma irradiation, the decellularized tissue samples produced by the D1 become destabilized, the onset denaturation temperature $T_d$ decreases to 46.2±1.6° C., and the peak denaturation temperature $T_d$ decreases to 51.2±1.8° C. This is a shift of thermal stability by 15° C. The decellularized tissue samples produced by any of the three protocols disclosed by the Application method are highly tolerant to gamma irradiation, the onset $T_d$ is >53° C. and registers a shift of thermal stability only by 3° C. The shape of thermograms of tissue samples produced by the Application method is also quite different from that of the D1 samples.

Therefore, tissue matrices made with the D1 method and the Application method have significantly different thermal stability.

6. Content of Collagen, Elastin and Saccharides

Table 4 shows the contents of collagen, elastin and saccharides in tissue samples produced by the D1 method and the Application method. Tissue matrices produced by the D1 method have significantly lower collagen content than those made by the Application method, i.e., 79.2±2.1% versus 88.0±2.8%, 89.4±2.7% and 89.5±2.6% for RJ-1, RJ-2 and RJ-3 of the Application protocols, respectively. Tissue matrices produced by the D1 method have significantly higher elastin and saccharides content. Therefore, the D1 method is much less effective than the Application method in removing non-collagenous elements.

TABLE 4

The content of collagen, elastin and saccharides in tissue matrices made with different methods

| Method | Collagen (%) | Elastin (%) | Saccharides (%) |
|---|---|---|---|
| D1 | 79.2 ± 2.1% | 3.1 ± 0.5% | 0.82 ± 0.05% |
| RJ-1 | 88.0 ± 2.8% | 2.1 ± 0.5% | 0.66 ± 0.02% |
| RJ-2 | 89.4 ± 2.7% | 2.4 ± 0.1% | 0.61 ± 0.06% |
| RJ-3 | 89.5 ± 2.6% | 1.5 ± 0.1% | 0.66 ± 0.06% |

\* The values are the mean ± SD.
N = 3.

7. The Resistance of Tissue Matrices to Collagenase and Trypsin

Figure 15:
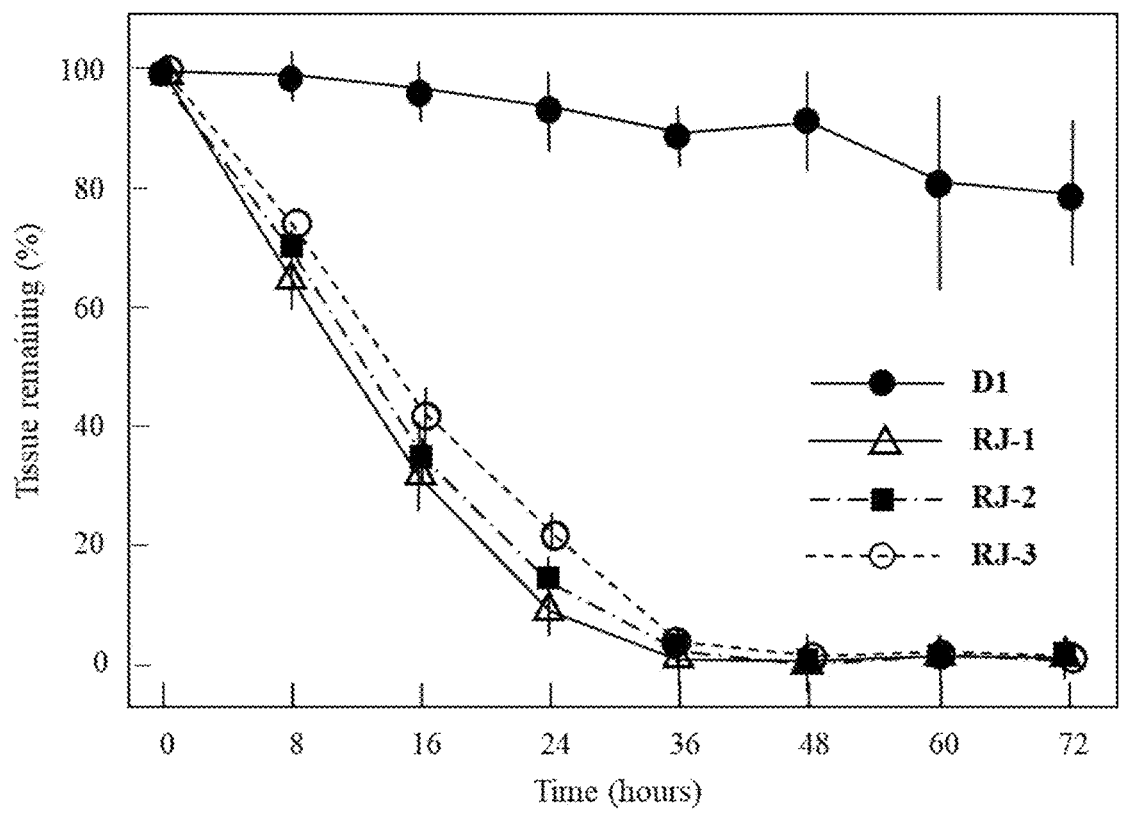
FIG. 15: The resistance to collagen degradation of tissue matrices derived from porcine dermis by the Methods of D1 and the Application.

FIG. 15 shows the resistance to type I collagenase of tissue matrices produced by the D1 method and the Application method. Tissue matrices produced by the D1 method are highly resistant to collagenase, only ~20% being degraded after treatment for 72 hours. Tissue matrices made by the Application method are reduced to ~50% within 15 hours.

Figure 16:
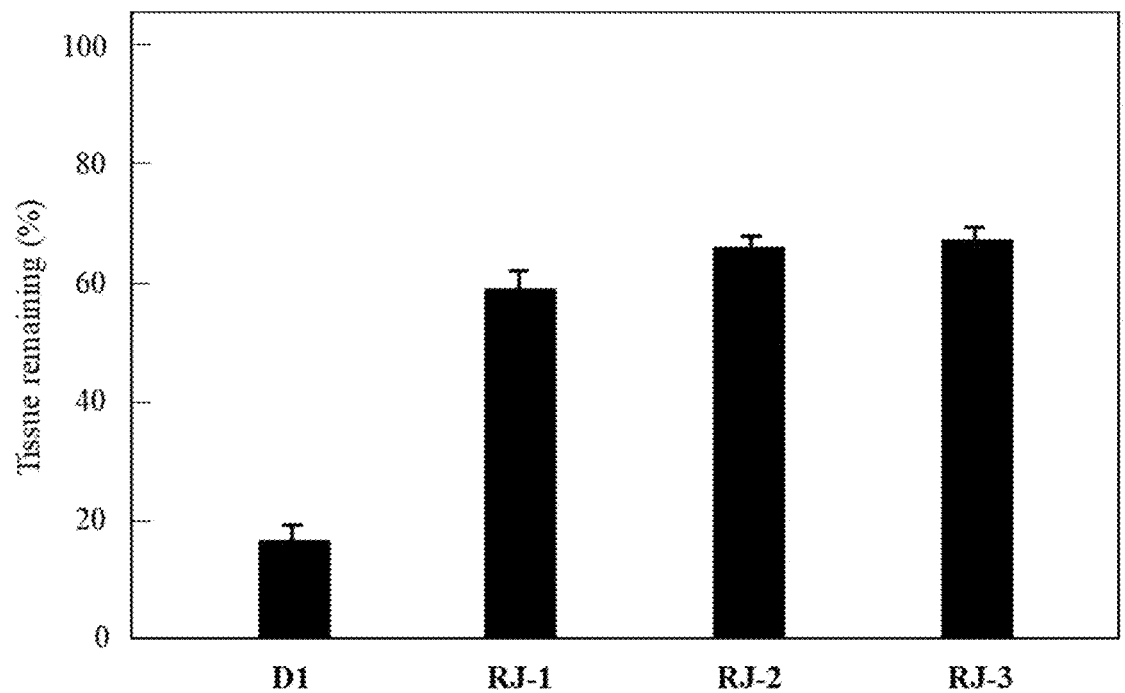
FIG. 16: The resistance to trypsin degradation of tissue matrices derived from porcine dermis by the Methods of D1 and the Application.

FIG. 16 shows the resistance to trypsin of tissue matrices produced by the D1 method and the Application method. Unlike the collagenase treatment, tissue matrices produced by the D1 method are significantly more susceptible to trypsin than tissue matrices produced by the Application method. Trypsin specifically cleaves proteins at carboxylic groups of exposed lysine and arginine. Trypsin can solubilize more than 80% of tissue matrices produced by the D1 method, suggesting a massive structural disruption in the tissue product produced by the D1 method.

8. Tensile Properties of Tissue Matrices

Figure 17A:
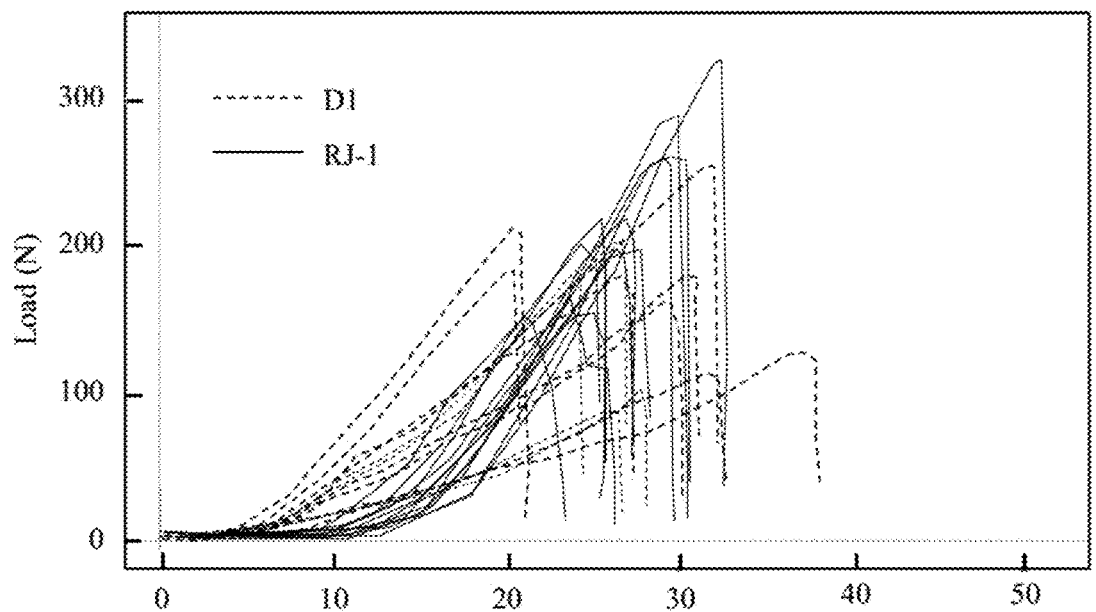
FIGS. 17A-17B: The tensile testing curves of tissue matrices derived from porcine dermis by the Methods of D1 and the Application.
Figure 17B:
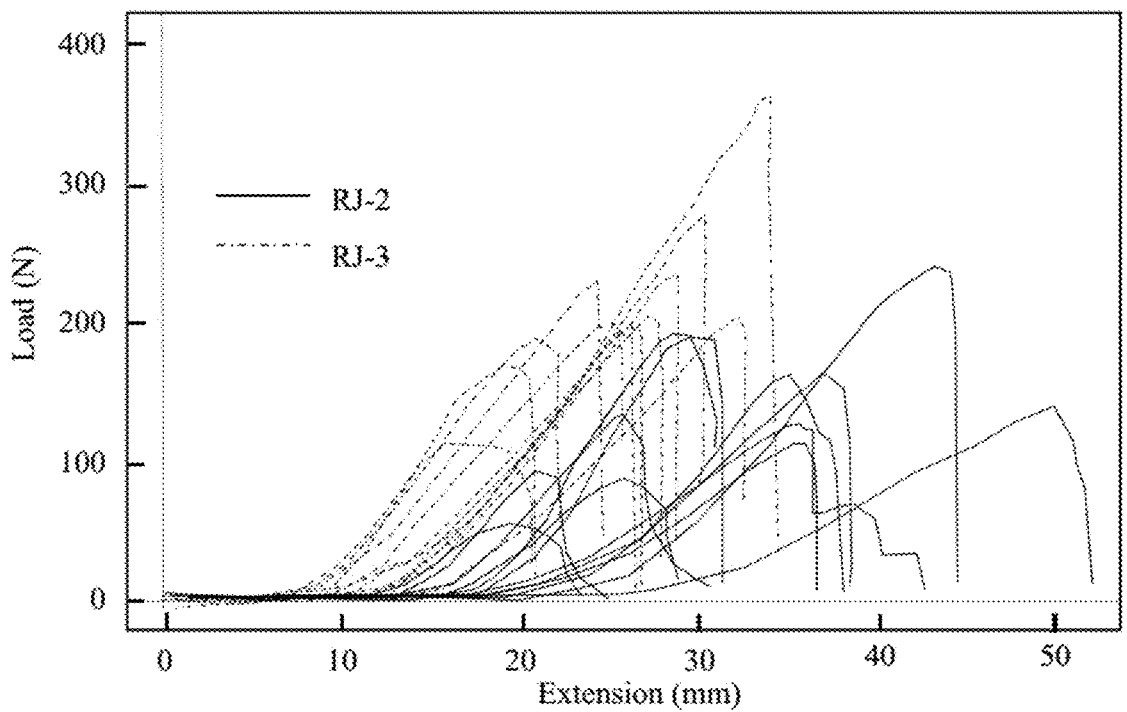

FIGS. 17A and 17B show the tensile testing curves of tissue matrices produced by the D1 method and the Application method. The forces (N) to pull the samples are plotted against the extension (mm) with an original gauge length of 40 mm. Table 5 shows four parameters describing these curves of tensile properties, including the % extension (strain) at 5N, the maximal break strength (N), the maximal % extension and the Young's modulus (MPa).

TABLE 5

Tensile properties of tissue matrices made with different methods

| Method | Strain at 5N (%) | Maximal load (N/cm) | Break strain (%) | Young's modulus |
|---|---|---|---|---|
| D1 | 14.8 ± 3.1 | 150 ± 47 | 69 ± 12 | 24.6 ± 8.8 |
| RJ-1 | 43.5 ± 10.8 | 137 ± 52 | 80 ± 3 | 34.8 ± 14.6 |
| RJ-2 | 27.2 ± 4.6 | 216 ± 54 | 66 ± 9 | 50.9 ± 7.1 |
| RJ-3 | 24.0 ± 5.7 | 210 ± 59 | 65 ± 12 | 44.8 ± 5.4 |

\* Values are the mean ± SD.
N = 12 (four test samples from each of three animals).

It is noted that the tensile testing curves exhibit large variations, as normally expected from biological samples.

Tissue matrices produced by the D1 method are less elastic than the tissue material produced by the Application method, as shown by the low stain value (%) at a load of 5N and the low Young's modulus. With a small N value of 12 measurements for individual methods, we cannot conclude with high certainty whether the observed differences in maximal load and break strain (%) represent practical significance in tensile parameters.

CONCLUSION

This comparative study has revealed a number of major differences in the acellular tissue matrices derived from the porcine skin material with the D1 method and the method of the application.

Major structural differences are shown by gross appearance, tissue pliability, histology, immuno-histopathology and SEM ultra-structures, as well as thermal stability of tissue matrices. Major differences in biochemical compositions also exist, including the contents of collagen, elastin, saccharides in tissue matrices. These major structural and compositional differences have resulted in drastically-different and biologically-relevant degradation patterns as demonstrated by the discrete resistance to type I collagenase and trypsin.

What is claimed is:

1. An animal acellular tissue matrix material which is manufactured by the method comprising the steps of:
   (1) collecting a raw material of an animal tissue, wherein the animal tissue is washed to remove blood and dirt, and cut into a tissue material having a length, a width and a height of the desired specification and dimension, and then the tissue material is preserved at a low temperature below freezing;

(2) thawing slowly, and rehydrating the tissue material from step (1) in normal saline containing gentamicin;
(3) disinfecting and sterilizing the tissue material from step (2) in a moderate alkaline solution, then rinsing the tissue material with sterile pure water, and adjusting the pH of the tissue material to be neutral, wherein the moderate alkaline solution is a sodium bicarbonate or sodium hydroxide solution with a pH of 10.5 to 11.5 or an ammonia hydroxide solution with a concentration of 0.1%, wherein in the step of disinfection and sterilization, the rehydrated tissue material is soaked in the moderate alkaline solution for 24 hours to 48 hours with slow shaking;
(4) decellularizing and washing the tissue material from step (3),
wherein the decellularizing comprises rinsing the disinfected, sterilized and rinsed tissue material in normal saline containing 2.0 mmol/L of calcium chloride, 2.0 mmol/L of magnesium chloride and 100 mg/L of gentamicin at room temperature for 1-3 hours, and then adding a dispase solution to remove the cells, wherein the dispase solution is a neutral dispase solution, containing 1 mmol/L to 20 mmol/L of calcium chloride, 1 mmol/L to 20 mmol/L of magnesium chloride and 50 units/L to 400 units/L of dispase, and the tissue material is soaked in the neutral dispase solution at 37° C. for 24 hours to 36 hours with slow shaking;
wherein the washing comprises washing with a first detergent solution at 37° C. for 12 hours to 18 hours with slow shaking and/or washing with a second detergent solution at room temperature for 24 hours to 36 hours with slow shaking, wherein the first detergent solution is prepared by dissolving polyethylene glycol tert-octylphenyl ether, at a concentration of 0.5%, in a buffer solution of hydroxyethylpiperazine ethane sulfonic acid with a pH between 7.0 and 8.0; and the second detergent solution is prepared by dissolving sodium deoxycholate, at a concentration of 1.0%, in phosphate buffer solution with a pH between 7.2 and 7.8;
(5) digesting DNA components of the animal tissue, wherein the animal tissue is then rinsed with normal saline;
(6) digesting α-Gal antigen of the animal tissue, wherein the animal tissue is then rinsed with 2% to 5% high concentration sodium chloride solution, and then rinsed with normal saline, and when the raw material of the animal tissue which has been improved by genetic engineering to have no α-Gal antigen, step (6) is omitted and step (7) is directly performed;
(7) inactivating any viruses in the tissue material and then rinsing the tissue material;
(8) packaging and sealing the tissue material under an aseptic condition; and
(9) terminal sterilization treatment of the tissue material to obtain the animal acellular tissue matrix material;
wherein an enzymatic method is used to remove cell components and α-Gal antigen and improve the flexibility of a scaffold.

2. The animal acellular tissue matrix material according to claim 1, wherein the washing of the animal tissue to remove blood and dirt in step (1) is performed by using pure water and a physical method or an ultrasonic method, or wherein the tissue material obtained in step (1) is preserved at a temperature of −40° C. or less which is achieved with an average cooling rate of no more than 1.0° C. per minute or the average cooling rate is 0.5° C. per minute.

3. The animal acellular tissue matrix material according to claim 1, wherein the preservation at a low temperature in step (1) is long-term; the tissue material is placed on a piece of protective layer of cotton yarn cloth, paper, plastic film, nylon net or suitable cloth fabric with an area larger than that of the tissue material, and roll the tissue material and the protective layer into one multilayer concentric roll or form a multilayer package form with the tissue material and the protective layer being alternated; the multilayer concentric roll or the multilayer package form is placed into a bag; and cryopreserved at −80° C. to −40° C. after being sealed.

4. The animal acellular tissue matrix material according to claim 1, wherein the tissue material preserved at a low temperature is thawed slowly in an environment of 5° C. to 12° C. in step (2), or wherein the thawed tissue material is rehydrated in a normal saline containing 100 mg of gentamicin per litre in step (2).

5. The animal acellular tissue matrix material according to claim 1, wherein the neutral dispase solution contains 2.0 mmol/L of calcium chloride, 2.0 mmol/L of magnesium chloride and 100 units/L to 200 units/L of dispase.

6. The animal acellular tissue matrix material according to claim 1, wherein after being soaked in the first detergent solution and/or the second detergent solution, and prior to step (5), the tissue material is rinsed three times with a buffer solution of 20 mmol/L of hydroxyethylpiperazine ethane sulfonic acid with a pH between 7.0 and 8.0 at room temperature, each time for 2 hours to 4 hours.

7. The animal acellular tissue matrix material according to claim 1, wherein digesting DNA components of the animal tissue in step (5) is accomplished by soaking the tissue material in a deoxyribonuclease solution for 18 hours to 28 hours with slow shaking, and then rinsing the tissue material twice in normal saline at room temperature, each time for 1 hours to 3 hours, wherein the deoxyribonuclease solution is prepared by adding 2.0 mmol/L of calcium chloride, 2.0 mmol/L of magnesium chloride and 5000 enzyme units/L of deoxyribonuclease into a buffer solution of 100 mmol/L of tri-hydroxymethyl aminomethane-hydrochloric acid with a pH of 7.2.

8. The animal acellular tissue matrix material according to claim 1, wherein digesting α-Gal antigen of the animal tissue in step (6) is accomplished by soaking the tissue material in an α-galactosidase solution and then washing the tissue for 24 hours to 36 hours with slow shaking, wherein the α-galactosidase solution is prepared by adding 2.0 mmol/L of calcium chloride, 2.0 mmol/L of magnesium chloride and an amount of 400 GALU units/L of α-galactosidase into a buffer solution of 10 mmol/L of hydroxyethylpiperazine ethane sulfonic acid with a pH between 7.0 and 8.0.

9. The animal acellular tissue matrix material according to claim 1, wherein the rinsing step of step (6) is to soak the tissue material in a 3% high concentration sodium chloride solution and wash the tissue material twice at room temperature, each time for 2 hours to 4 hours.

10. The animal acellular tissue matrix material according to claim 1, wherein agents used in the virus inactivation in step (7) are hydrogen peroxide and peroxyacetic acid, and in the step of the virus inactivation, the tissue material is soaked in a solution containing 0.01% to 0.10% hydrogen peroxide, 0.05% to 0.50% acetic acid and 0.05% to 0.50% peroxyacetic acid, and then is washed for 2 hours to 3 hours at room temperature with slow shaking.

11. The animal acellular tissue matrix material according to claim 1, wherein after the virus inactivation in step (7), the tissue material is rinsed three times at room temperature with a neutral phosphate buffer solution, each time for 2 hours to 4 hours.

12. The animal acellular tissue matrix material according to claim 1, wherein the terminal sterilization treatment in step (9) is to perform the sterilization treatment by using low temperature gamma ray irradiation or ethylene oxide gas, with the treatment dosage of gamma ray being 10 kGy to 50 kGy.

13. The animal acellular tissue matrix material according to claim 1, wherein the sequence of step (4), step (5) and step (6) can be adjusted as required.

14. The animal acellular tissue matrix material according to claim 1, wherein the animal acellular tissue matrix material are reduced to about 50% within 15 hours by collagenase.

15. The animal acellular tissue matrix material according to claim 1, wherein the animal acellular tissue matrix material is softer than unprocessed matrix material.

16. The animal acellular tissue matrix material according to claim 1, wherein the animal acellular tissue matrix material stains negative for Lectin I isolectin B4.

17. The animal acellular tissue matrix material according to claim 1, wherein the animal acellular tissue matrix material is tolerant to gamma irradiation, wherein the onset denaturation temperature $T_d$ is >53° C. and there is a shift of thermal stability by 3° C. in reference to the acellular tissue matrix material prior to terminal sterilization step (9) of claim 1.

18. The animal acellular tissue matrix material according to claim 1, wherein the animal acellular tissue matrix material has a collagen content of 88.0±2.8% of the total dry weight of the animal acellular tissue matrix material, the animal acellular tissue matrix material has a collagen content of 89.4±2.7% of the total dry weight of the animal acellular tissue matrix material, or the animal acellular tissue matrix material has a collagen content of 89.5±2.6% of the total dry weight of the animal acellular tissue matrix material.

19. The animal acellular tissue matrix material according to claim 1, wherein the animal acellular tissue matrix material is ~50% degraded by collagenase within 15 hours.

* * * * *